(12) United States Patent
Vetter et al.

(10) Patent No.: US 12,004,727 B2
(45) Date of Patent: Jun. 11, 2024

(54) SOFT AND HARD TISSUE EXCISIONAL DEVICES AND METHODS

(71) Applicant: TransMed7, LLC, Portola Valley, CA (US)

(72) Inventors: Eugene H Vetter, Portola Valley, CA (US); James W Vetter, Portola Valley, CA (US)

(73) Assignee: TransMed7, LLC, Portola Valley, CA (US)

( * ) Notice: Subject to any disclaimer, the term of this patent is extended or adjusted under 35 U.S.C. 154(b) by 815 days.

(21) Appl. No.: 17/153,582

(22) Filed: Jan. 20, 2021

(65) Prior Publication Data

US 2021/0251615 A1 Aug. 19, 2021

Related U.S. Application Data

(63) Continuation of application No. 16/000,047, filed on Jun. 5, 2018, now abandoned.

(51) Int. Cl.
*A61B 10/02* (2006.01)
*A61B 10/06* (2006.01)
(Continued)

(52) U.S. Cl.
CPC .......... *A61B 10/0266* (2013.01); *A61B 10/06* (2013.01); *A61B 17/3207* (2013.01);
(Continued)

(58) Field of Classification Search
CPC . A61B 10/0266; A61B 10/06; A61B 17/3207; A61B 2010/0208;
(Continued)

(56) References Cited

U.S. PATENT DOCUMENTS 9,826,976 B2 * 11/2017 Parihar ................ A61B 17/068
2005/0054947 A1 * 3/2005 Goldenberg ....... A61B 10/0266
600/567
(Continued)

*Primary Examiner* — Alex M Valvis
*Assistant Examiner* — Justin Xu
(74) *Attorney, Agent, or Firm* — YOUNG LAW FIRM, P.C.

(57) ABSTRACT

A device may comprise a work element, an outer tube co-axially disposed around a portion of the work element and a collar assembly. The work element may be configured to rotate and define proximal and distal ends, and may comprise a body portion, one or more articulable beak(s) configured to cut tissue, and a beak actuation portion. The collar assembly may be coupled to the work element away from the articulable beak(s), and may comprise a distal collar element coupled to the body portion, a middle collar element coupled to the outer tube and a proximal collar element coupled to the beak actuation portion. The distal collar element may comprise a first peripheral surface that extends around the distal collar element and that faces the proximal end and the middle collar element may comprise a second peripheral surface that that extends around the middle collar element, faces the distal end and at least partially contacts the first peripheral surface. The first and second peripheral surfaces each may comprise a smooth undulating surface that comprises a plurality of peaks and valleys. The distal, middle and proximal collar elements may be configured to control opening, closing, extending and retracting the articulable beak(s) by rotating in synchronicity, rotating differentially and/or moving toward the distal or proximal ends.

9 Claims, 18 Drawing Sheets

(51) Int. Cl.
    *A61B 17/00*         (2006.01)
    *A61B 17/32*         (2006.01)
    *A61B 17/3207*     (2006.01)

(52) U.S. Cl.
    CPC ............. *A61B 2010/0208* (2013.01); *A61B 2017/00473* (2013.01); *A61B 2017/00685* (2013.01); *A61B 2017/320064* (2013.01); *A61B 2217/005* (2013.01)

(58) Field of Classification Search
    CPC  A61B 2017/00473; A61B 2017/00685; A61B 2017/320064; A61B 2217/005
    See application file for complete search history.

(56) References Cited

U.S. PATENT DOCUMENTS

| | | | | |
|---|---|---|---|---|
| 2011/0313316 A1* | 12/2011 | Ranpura | ............ | A61B 10/0275 600/566 |
| 2012/0109171 A1* | 5/2012 | Zeroni | ............ | A61B 17/320758 606/159 |
| 2016/0089121 A1* | 3/2016 | Stand, III | ............ | A61B 10/0266 74/89.23 |
| 2017/0056040 A1* | 3/2017 | Vetter | ................ | A61B 10/0233 |

* cited by examiner

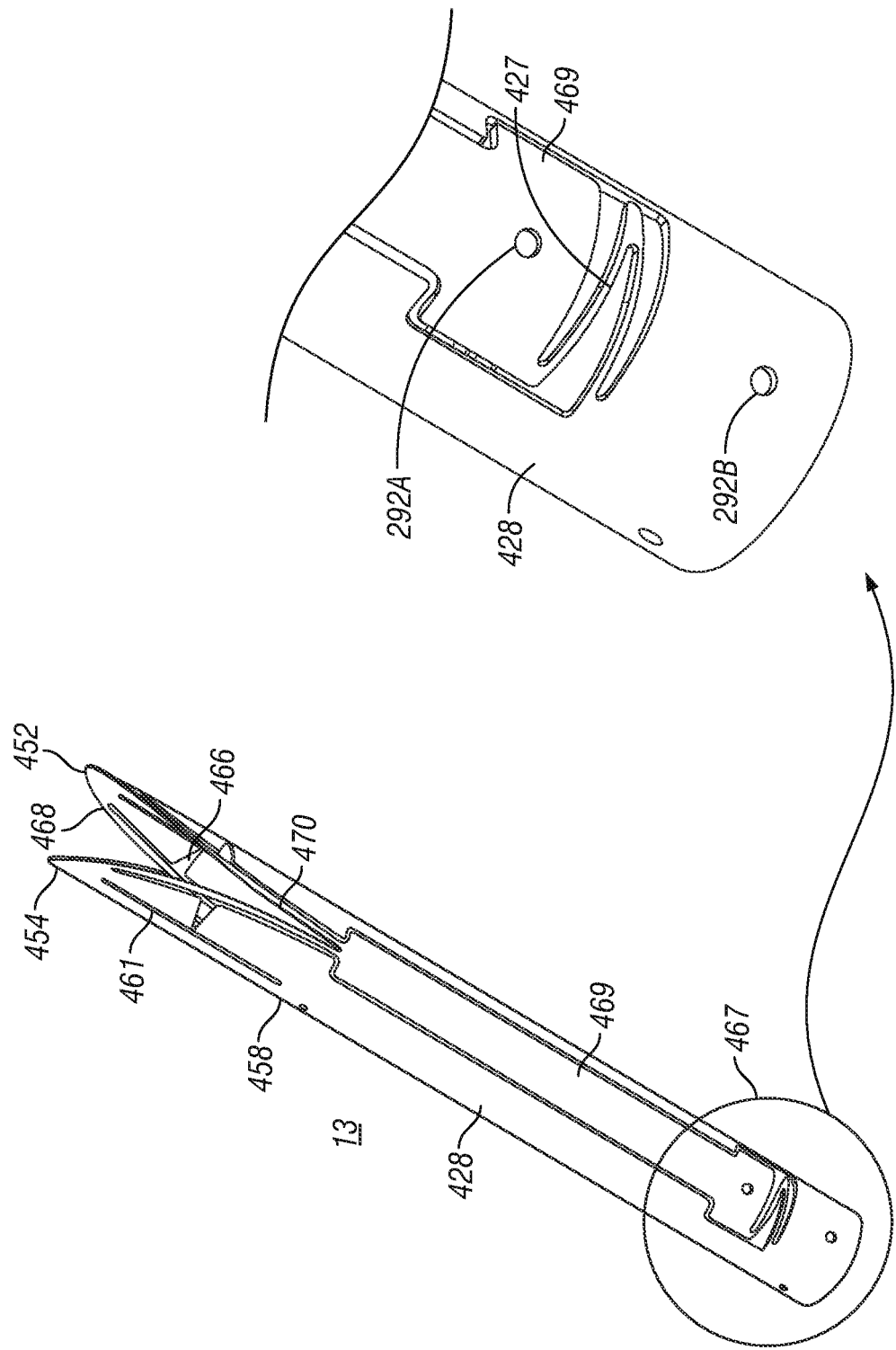

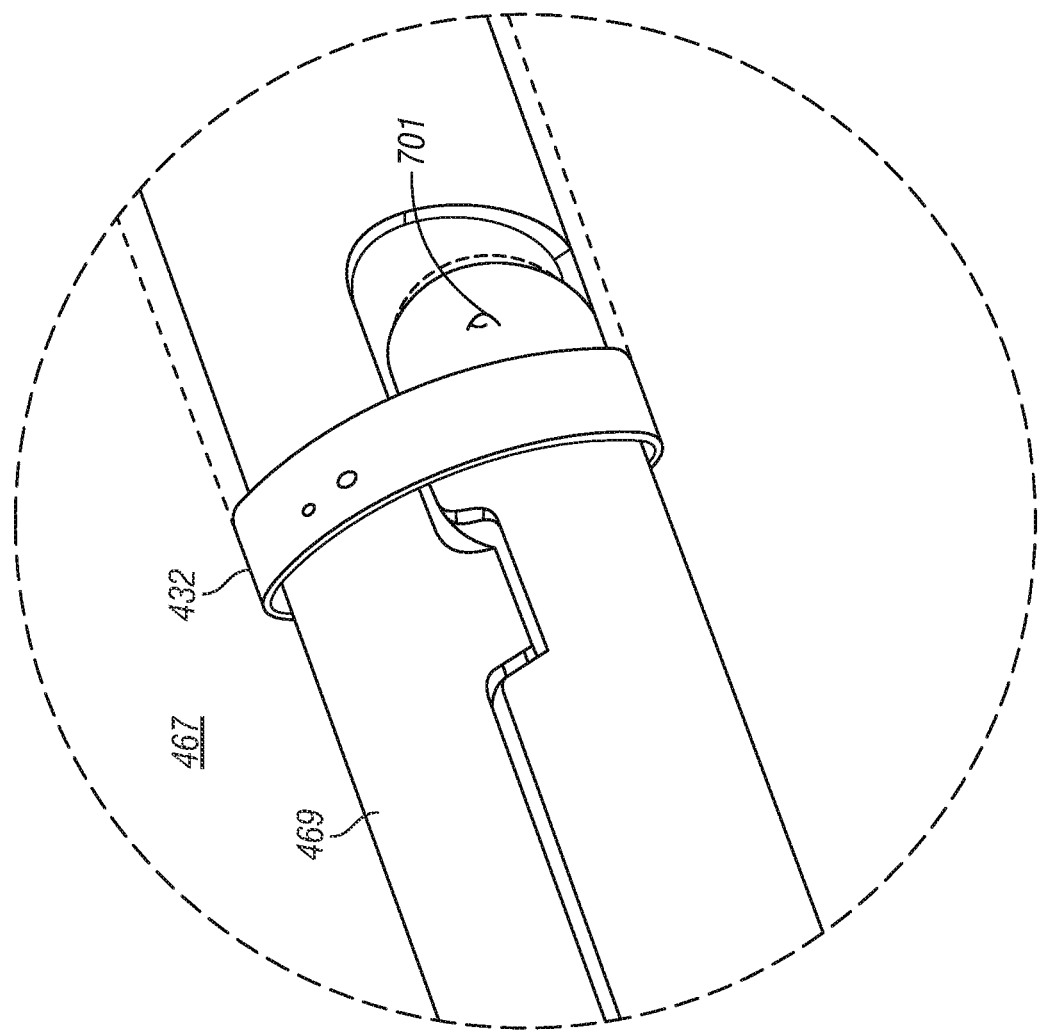

SOFT AND HARD TISSUE EXCISIONAL DEVICES AND METHODS

CROSS-REFERENCE TO RELATED APPLICATIONS

The present application is related in subject matter to commonly assigned and co-pending U.S. patent application Ser. No. 14/864,146 filed 24 Sep. 2015 (CORSAIR), now U.S. Pat. No. 10,736,651 and Ser. No. 14/599,481 filed 21 Jan. 2015 (CORSAIR2), now U.S. Pat. No. 10,231,750, U.S. patent application Ser. No. 13/973,898, now U.S. Pat. No. 9,155,527; U.S. patent application Ser. No. 14/050,771, now U.S. Pat. No. 10,806,434; U.S. patent application Ser. No. 14/852,969, now U.S. Pat. No. 10,076,315; U.S. patent application Ser. No. 14/852,901, now U.S. Pat. No. 9,999,758; and U.S. patent application Ser. No. 14/484,122, now U.S. Pat. No. 10,555,751, the entire disclosures of which are hereby incorporated herein in their entirety.

BACKGROUND

Embodiments relate to medical devices and methods. More particularly, embodiments relate to hand-held or mounted single or multiple insertion, single or multiple excisional devices and corresponding methods for vascular clearing and restoration applications. Embodiments further relate to improvements over currently used chronic total occlusion removal systems, specifically in providing minimally invasive and more widely capable and reliable cardio-vascular excisional devices and methods. Embodiments further relate to improvements over currently used orthopedic material removal systems and methods.

SUMMARY

Embodiments are drawn to various medical devices and methods that may be used for intra-vascular and skeletal or bone marrow biopsy procedures. According to one embodiment, an excisional device may be configured to remove liquids, solids, semi-solids and single or multiple material samples during a single insertion through the skin (percutaneous procedure) into any vascular area of the body, as well as for clearing any other occluded vessel. Embodiments may comprise structures and functionality for different phases of a multi-phase vascular clearing or restoration procedure, which may be performed by hand or by device attachment to an imaging stage. Embodiments may also comprise devices configured for insertion through the central lumen of another compatible excisional device. Embodiments of a device, along with associated related subcomponents described herein, may provide the capability to retrieve solid, contiguous and/or fragmented materials as well as liquid and semi-solid tissues for analysis, diagnosis and treatment and exhibit improvements in functionality and performance relative to present devices and methods for clearing chronic total occlusions and other vascular anomalies. Although some embodiments may find particular utility in cardio-vascular intervention procedures, other embodiments may also find utility in, for instance, musculo-skeletal or neurologic applications, and are not limited therefore to vascular applications described, shown and claimed herein. Embodiments and elements thereof may be deployed in interventional procedures in coronaries, including bypass vessels (veins, internal mammary arteries, free radial grafts and in the case of peripheral vessels, synthetic grafts, native and bypass peripheral vessels including carotid arteries, renals, iliacs, femorals and distal vessels including venous and arterial vessels in various locations). Embodiments may include atherectomy and thrombectomy devices (those that remove plaque and other components of diseased vessel walls), which may also contain a subset that may be used to treat both acute and chronic thromboembolic lesions and another subset that may be used to remove restenotic "scar" tissue obstructions (intimal hyperplastic lesions); chronic total occlusion devices, which include a variety of devices some of which may be considered variants of atherectomy devices and finally, delivery devices to deliver medications, implants, and devices such as other interventional devices performing functions listed above as well as guiding elements including catheters and various types of guiding and interventional wires, imaging catheters and wires, contrast media, oxygenation elements, sensing instruments, radiation delivery elements, protective and shielding devices, downstream safety devices and others. Embodiments may be configured to be portable, disposable or reusable and may be, for example, electrically/electronically-, mechanically-, hydraulically-, pneumatically- and/or manually-, powered, controlled and operated.

According to one embodiment, a device for material excision or removal from vascular or skeletal structures for either handheld or stereotactic table use may comprise a work element or elements configured to selectively open and close at least one articulable beak configured to penetrate and remove intra-vascular materials or obstructions, or follow a central lumen of another device or over a wire in a longitudinal direction. Flush and vacuum tissue transport mechanisms may be incorporated. An inner sheath and an outer sheath, which may be co-axially disposed relative to a work element, may be configured to actuate a beak or beaks for simultaneous beak closing under rotation.

One embodiment is a device that may comprise a work element configured to rotate and defining a proximal end and a distal end away from the proximal end, the work element comprising a body portion, at least one articulable beak disposed at a distal end of the body portion and configured to cut tissue, and a beak actuation portion; an outer tube co-axially disposed around a portion of the work element; and a collar assembly coupled to the work element away from the at least one articulable beak, the collar assembly comprising at least a distal collar element coupled to the body portion of the work element, a middle collar element coupled to the outer tube and a proximal collar element coupled to the beak actuation portion, the distal collar element comprising a first peripheral surface that extends around the distal collar element and that faces the proximal end, the middle collar element comprising a second peripheral surface that that extends around the middle collar element, faces the distal end and at least partially contacts the first peripheral surface. The first peripheral surface may be a smooth surface that comprises a plurality of first peaks and a plurality of first valleys and the second peripheral surface may be a smooth surface that comprises a plurality of second peaks and a plurality of second valleys. The distal, middle and proximal collar elements may be configured to control opening, closing, extending and retracting the at least one articulable beak by rotating in synchronicity, rotating differentially, moving toward the distal end and/or moving toward the proximal end.

According to other embodiments, the work element may be a single tube-shaped piece of material comprising a plurality of cuts therein that defines the at least one articulable beak, the body portion and the beak actuation portion. The outer tube may be configured to rotate relative to the body portion of the work element to cause the first and second peripheral surfaces to slide against one another and the at least one articulable beak to cyclically open and close. The outer tube may be configured for limited travel in a distal or proximal direction and pulling the outer tube in the proximal direction relative to the work element may cause the middle collar element to pull the proximal collar in the proximal direction and to close the at least one articulable beak.

The body portion of the work element may be configured for limited travel in the distal or proximal direction and pushing the body portion in the distal direction relative to the outer tube may cause the distal collar element to move distally relative to the middle collar and to close the at least one articulable beak. Differential rotation of the body portion relative to the outer tube cyclically may open and close the articulable beak(s). Differential rotation of the distal and middle collars may cause the first peaks and first valleys of the first peripheral surface to slide against the second peaks and second valleys of the second peripheral surface. Differential axial movement of the body portion relative to the outer tube may cyclically at least partially open or close the articulable beak(s). A first profile defined by the first peaks and first valleys of the first peripheral surface and a second profile defined by the second peaks and second valleys of the second peripheral surface may define a pattern, upon rotation of at least the collar assembly, of at least partial opening and at least partial closing the at least one articulable beak in operation of the device. The differential rotation of the body portion relative to the outer tube may define a rate at which the articulable beak(s) cyclically at least partially open and close. The collar assembly may be further configured such that axially-directed pulsed movement of at least the collar assembly causes the at least one articulated beak to undergo a jackhammer-like reciprocating motion in at least a partially opened or in at least a partially closed configuration. The depth of the first and second valleys and the height of the first and second peaks may define the degree to which the at least one articulable beak cyclically opens and closes as the peripheral surfaces of the distal and middle collar elements slide against each other. The first peripheral surface may match the second peripheral surface such that the first peripheral surface mates in intimate contact with the second peripheral surface at least once each time one of the first and second peripheral surfaces fully rotates around the other of the first and second peripheral surface.

Another embodiment is a device, comprising a work element configured to rotate and defining a proximal end and a distal end away from the proximal end, the work element comprising a body portion, one or more articulable beaks disposed at a distal end of the body portion and configured to cut tissue, and a beak actuation portion; a proximal sheath comprising a resilient portion near a distal end thereof, the proximal sheath being coupled to the beak actuation portion of the work element; a distal sheath partially disposed over the work element and coupled to the proximal sheath distally relative to the resilient portion thereof; and a collar assembly coupled to the work element away from the articulable beak(s), the collar assembly comprising at least a first collar element coupled to the body portion of the work element and a second collar element coupled to the distal sheath, the first collar element comprising a first peripheral surface that extends around the first collar element and that faces the proximal end and the second collar element comprising a second peripheral surface that that extends around the second collar element, faces the distal end and at least partially contacts the first peripheral surface. The first peripheral surface may be a smooth surface that comprises a plurality of first peaks and a plurality of first valleys and the second peripheral surface may be a smooth surface that comprises a plurality of second peaks and a plurality of second valleys. The proximal sheath, the distal sheath and the collar assembly may be configured to control opening, closing, extending and retracting the articulable beak(s) by rotating in synchronicity, rotating differentially, moving toward the distal end and/or moving toward the proximal end.

According to further embodiments, the work element may be a single tube-shaped piece of material comprising a plurality of cuts therein that defines the at least one articulable beak, the body portion and the beak actuation portion. Differential rotational motion of the distal tube and of the proximal tube may be configured to cause the first and second peripheral surfaces to slide against one another and the articulable beak(s) to cyclically open and close. The distal tube may be configured for limited travel in a distal or proximal direction and pulling the distal tube in the proximal direction relative to the work element may cause the second collar element to pull the proximal sheath in the proximal direction and to close the articulable beak(s). Differential rotation of the distal tube relative to the proximal tube may cyclically open and close the articulable beak(s). Differential rotation of the first and second collars causes the first peaks and first valleys of the first peripheral surface to slide against the second peaks and second valleys of the second peripheral surface. Differential axial movement of the distal sheath relative to the proximal sheath may cyclically at least partially open and close the articulable beak(s).

A first profile defined by the first peaks and first valleys of the first peripheral surface and a second profile defined by the second peaks and second valleys of the second peripheral surface may define a pattern of at least partial opening and at least partial closing the articulable beak(s) in operation of the device. A differential rotation of the distal sheath relative to the proximal sheath may define a rate at which the articulable beak(s) cyclically at least partially open and close. The distal sheath may be configured such that a periodic axial movement thereof causes the articulated beak(s) to undergo a jackhammer-like reciprocating motion in at least a partially opened or in at least a partially closed configuration. The depth of the first and second valleys and the height of the first and second peaks define a degree to which articulable beak(s) cyclically open and close as the peripheral surfaces of the first and second collar elements slide against each other. The first peripheral surface may match the second peripheral surface such that the first peripheral surface mates in intimate contact with the second peripheral surface at least once each time one of the first and second peripheral surfaces fully rotates around the other of the first and second peripheral surface.

According to one embodiment, a method may comprise providing a device comprising a work element configured to rotate and defining a proximal end and a distal end away from the proximal end, the work comprising, at the distal end thereof, at least one articulable beak configured to cut tissue; and a collar assembly coupled to the work element away from the at least one articulable beak. The collar assembly may comprise at least a first collar element comprising a first peripheral undulating surface that faces the proximal end and a second collar element comprising a second peripheral undulating surface that faces the distal end and that at least partially contacts the first peripheral undulating surface, the first and second collar elements being configured to rotate in synchronism or differentially relative to one another. At least the work element may then be rotated and at least the distal end of the work element inserted into tissue. The movements (rotational, axial) of at least the first and second collar elements may then be suitably and selectably controlled to at least partially open the articulable beak(s) to core through tissue; at least partially close the articulable beak(s) to dissect through tissue; cause cyclic at least partial openings and closings of the articulable beak(s) as the first and second peripheral undulating surfaces slide against one another; and/or cause cyclic short excursions of the articulable beak(s) toward the distal end and back toward the proximal end in a jackhammer-like motion.

In one embodiment, providing may be carried out with the work element being a single tube-shaped piece of material comprising a plurality of cuts to define the articulable beak(s).

BRIEF DESCRIPTION OF THE DRAWINGS

FIG. 2 shows a monolithic beak assembly of an excisional device according to one embodiment.
FIG. 3 shows a detail of a proximal end of a monolithic beak assembly of an excisional device according to one embodiment.
FIGS. 14A and 14B show details of a work element, according to one embodiment.

DETAILED DESCRIPTION

Figure 1:
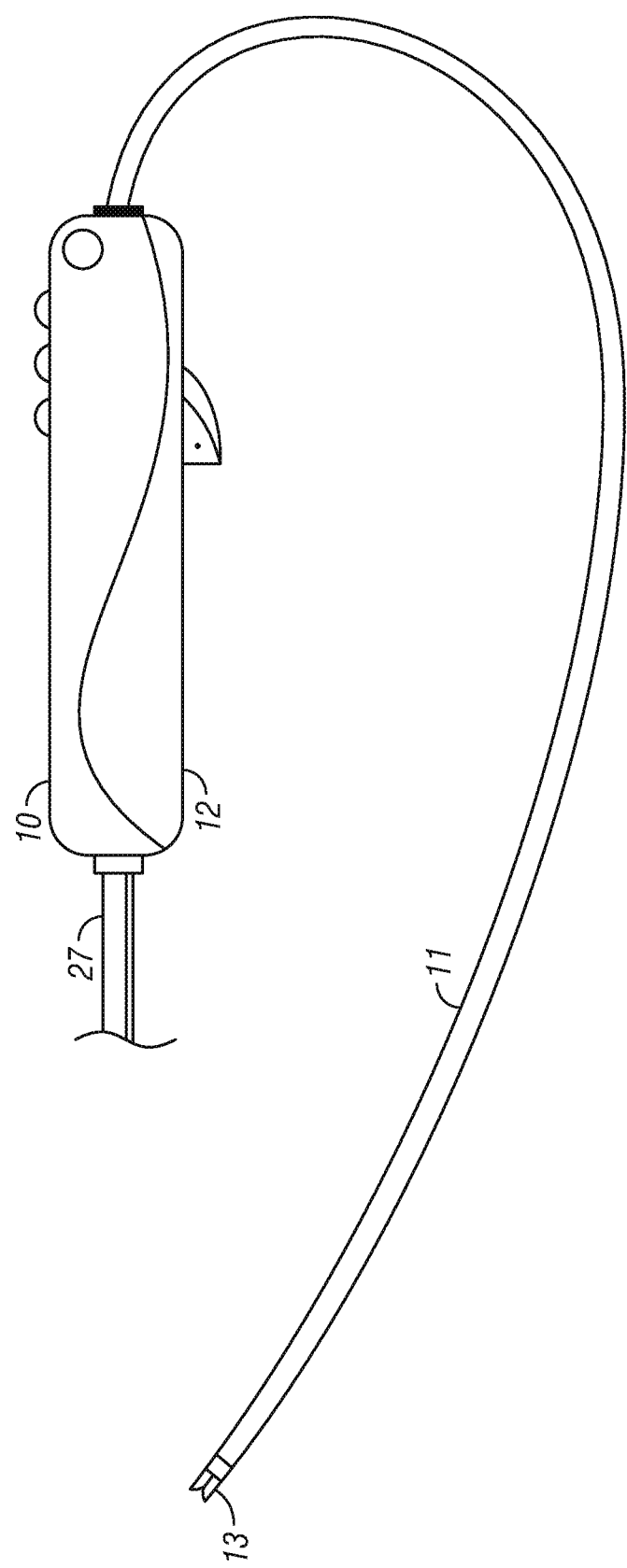
FIG. 1 is a perspective side view of an excisional device, according to one embodiment.

Reference will now be made in detail to the construction and operation of implementations of the embodiments illustrated in the accompanying drawings. The following description is only exemplary of the embodiments described and shown herein. The embodiments, therefore, are not limited to these implementations, but may be realized by other implementations.

According to embodiments, a device for material or tissue excision may be configured to remove intra-vascular or other materials in the fields of, for example, cardio-vascular, orthopedic or neurologic intervention, particularly wherein a system capable of cyclic morcellation in concert with or without cyclic forward jack-hammer motion, any combination of which may be under rotation at any appropriate speed, and removal of hard or soft tissue materials may be desirable, and may comprise a range of work element dimensions ranging from, for example, approximately 0.0065" to 0.249" diameter (⅓ French to 19 French), or other appropriate dimensions both larger and smaller depending on applications and field of use requirements. According to embodiments, an excisional device may comprise a generally flexible tubular structure, which may be at least partially disposed within a coaxially-disposed outer tube or tubes, which outer tube or tubes may comprise a fixed or removable distal scoopula(s) or beak(s). A work element, according to one embodiment, may comprise one or more scoopulas and/or one or more beaks. Either may be fixed or articulable, sharpened or unsharpened at their tips or along their side axes, and combinations of the two may be interchanged, according to embodiments. In the case of either articulable beaks or scoopulas, the principles of action as described herein and according to embodiments may be similar or different to that used for one relative to the other.

Beak (distal working end) actuation for the purposes of cycling between closed-state (for penetration and part-off) and wide open state (for coring and capturing tissue sample) while rotating can be accomplished with a push-pull mechanism that originates in a driving assembly far proximal to the beak structures themselves so long as the connection between a proximal driver and the movable structures including the movement of living backbone hinge elements relative to living hinge tendon/keystone elements of the beaks, is comprised of relatively rigid structures that can transmit small movements precisely, relying on column strength structural integrity combined with relatively inelastic tension structures to transmit these direct, linear forces over the length between the beaks and driver mechanism. This mechanism is successful for instruments that can rely on relatively rigid members between handle (driver) and working end but in the event the application requires a relatively long flexible catheter between driver (handle end) and working end, a simple proximal push-pull motion that is then required to be transmitted in a linear way along a tortuous pathway may be problematic. In fact, there are several factors that render linear motion transmission along the length of a flexible catheter undesirable as a way to transmit the precise forces needed to actuate the beak mechanisms to cycle between fully open and closed, since these distal motions may be as small as several thousandths of an inch, particularly when the catheter is forced into curves needed to gain access to a treatment site. As a result, it is highly advantageous to generate the push-pull forces needed to actuate the beaks locally, that is, as near the actual living-hinge backbone and living tendon members as possible, using forces that are less affected by flexing the catheter over or through which these forces are transmitted. One such exemplary mechanism is described below, although the important and basic concept is to utilize a mechanism that allows significant flexing of the catheter connecting driver and working distal end, while providing forces that may be converted to small, precise, repeatable linear push-pull forces locally—that is, at the distal end very near to keystone and backbone elements, the relative motion of which cycles open and closed the beak element(s)—while also enabling powered rotation of the beak elements for penetration (closed beak), coring (open beak), and part-off/transport (closed beak). It is also desirable to permit an open core transmission section between beak elements and storage chamber proximal to the driving mechanism. The exemplary mechanisms presented below fulfills these requirements although any other mechanism that also fulfills this specification would be considered of the same basic concept described.

Herein, beaks may refer to that portion of a work element whose primary functions may comprise coring, shaving or grasping to remove material, and may also be fixed, articulable, sharpened or unsharpened, and may have various features and shapes according to various embodiments. Beaks may comprise longitudinal living hinge elements such that the beaks may be expanded "out of round" to a more flattened shape, or alternatively a more tubular shape than when at rest. Beak driving assembly or assemblies in the device may have operating characteristics and features to enable rotational speeds advantageously chosen to optimize "sweep" ultrasound imaging using mechanical array or at a different speed to increase the information provided with phased array imaging, for example and may include longitudinal and "off angle" sweep capabilities as they are articulated to "shine" ultrasound or light energy at various structures of interest. These capabilities can also be used to receive signals in return and/or for reference signal processing. These capabilities can also be used together with "light out, sound in" systems that combine light and sound efferent and afferent signal processing to increase information available using a combination of these modalities. These rotational, longitudinal "pullback" and angular speeds may be generally in the same range as useful cutting, pullback/advancement and angular speeds, or they may be outside that normal range and activated separately for diagnostic or other therapeutic procedures (radiation delivery, medication "painting", injecting or other delivery). Driving assembly or assemblies (hereafter, collectively "driving assembly" for ease of reference) for beaks may be controllable at the handle end of the device (e.g., outside the body) and can be quite sophisticated, reusable and electronically optimized for torque, rotational speed (rpm) and frequency (in the cases of translation, angular changes and oscillation motions). The driving assembly may also comprise variable control as needed and may also include the ability to halt work element motions at a part-off phase (a phase at which a cut or cored piece of tissue or material is separated from surrounding tissue), with automated rearward (proximal) translation for purposes of delivering excised materials (e.g., pieces of tissue or material) to a transport portion of the device where, according to one embodiment, vacuum along with fluid management flows and swirls may complete the rearward delivery into a serial collection magazine of the device, and according to another embodiment, such vacuum and flush systems may be augmented with internal helice(s) or Archimedes screw type augers or variants thereof, as may be envisioned by one skilled in the art. Driving mechanisms may also include delivery of electrical, mechanical, radiant, ultrasonic, electromagnetic, electron beam and simple magnetic, among other, energies distally to a work element area, whereby conversion or re-conversion to another energy form may be made in the work area. As examples, electrical energy may be delivered to a receiving electromagnetic device to mechanically actuate a distal element, or turbine power generated may be transmitted distally via inert gases or mechanical spinning of elements acting directly on a distal element or simply via fluids that may be present or introduced in the presence of spinning elements according to embodiments, that may function to both create vacuum at the distal work element area while also creating mechanical motion in another or the same element, such as a high speed, low torque rotational element such that simultaneous dissolution and sucking of debris such as clotted blood or particulate matter rearward and safely out of the work area may be accomplished. Yet another example is that an e-beam sent distally may be directionally by elements in the work area in which case energy is precisely redirected and focused by embodiments, rather than converted to another form of energy per se. Multiple energies such as "light in, sound out" technologies among others, combining more than one modality to interrogate an area and supply more detailed information based on the modalities utilized in such a combination may be, at the same time, delivered, received and in some cases advantageously altered by elements of the present embodiments.

It is to be noted that, herein, the phrase "helical element" and the terms "helix" or "helices" are intended to encompass a broad spectrum of structures. Indeed, the structures shown herein are but possible implementations of a helical element, helix or helices. According to other embodiments, "helical element", "helix" or "helices" and equivalent expressions may be implemented as tubes having one or more slot-shaped openings or fenestrations along at least a portion of the length thereof. Such fenestrations may be substantially parallel to the longitudinal axis of a tube or may be disposed, for example, in a spiral configuration. The fenestrations may be continuous along at least a portion of the length of a tube or may be discontinuous, such as to result in a plurality of such parallel or spirally wound fenestrations. The fenestrations may be very wide such that the resultant structure resembles a spring, or more narrow, such that the resulting structure more closely resembles a tube having narrow, slot-shaped openings therein. The continuous or discontinuous fenestrations may be caused to assume other configurations along at least a portion of the tubes in which they are formed. For example, the fenestrations may be caused to form a zigzag pattern such as "NNNN . . . ", "ΛΛΛΛΛ " or "VVVV . . . " ΛΛΛΛΛ or a cross-shaped pattern, such as "XXXXX". Significantly, the terms "helical element," "helix," or "helices" should be understood to cover a spectrum of structures, from a spring-like structure to tubes having selected slot-shaped openings, with such tubes exhibiting rigid or flexible portions along their lengths.

Embodiments of devices comprising variations of scoopula(s) may be configured to isolate the working surface (s) from the flow surfaces. In use in a vascular lumen, for example, this means that the lumen and/or potential lumen (tight stenoses and complete occlusions, whether chronic or acute) space will be protected before and additionally as soon as there is sufficient space to permit blood flow, including gently forced flow for the purposes of downstream oxygenation and nutrition, introduction of imaging equipment, and natural flows based on driving pressures relieved by new or widened lumens. This space (the lumen space) is isolated from the working space so that any elements that are released during removal actions will be prevented from impairing flow in the protected flow lumen of the vessel being widened in caliber. This space will be utilized such that vacuum may be maximized in the working side of the vessel as defined by the scoopula, and also in certain embodiments, while protecting the flow side—an embodiment may simultaneously press against the wall on the flow side (opposite to the working side) causing the working side of a catheter to be pressed against the lesion side of the vessel so that the elements on the working side of a device may be held precisely at the desired depth (for example for removing as much or little of a lesion as may be optimal for various considerations such as transport, degree of aggressiveness, rate of removal, particulate size of the material being removed, as the working beak element(s) are given purchase). Embodiments also provide a stable, geometrically straight reference platform. This reference platform may be used to straighten a desired segment of a vessel such that a uniform depth of lesion material may be safely removed without the concern for asymmetrically removing deep-wall elements (for example in an otherwise naturally or as a result of disease, tortuous section of a vessel) that may lead to weakening, aneurism formation or even perforation during the procedure.

As used throughout this disclosure, work elements may comprise one or more tubes, and the terms "inner" and "outer" tubes may be used with reference to a single work element, or in reference to two or more co-axially located work elements (or "complex work elements", as used herein), each of which may comprise one or more tubes to enable their specific function. A coaxially-disposed outer tube, according to one embodiment, may also comprise one or more coatings. According to one embodiment, a tube may comprise a stainless-steel hypodermic tubing ("hypo tube"). Such a stainless hypo tube, according to one embodiment, may be provided with (e.g., laser) cuts to define a monolithic distal assembly that defines beaks, a living hinge that attaches the beak(s) to the generally tubular body of the device or that homogeneously spans between the beak(s) and the generally tubular body of the device. According to one embodiment, cuts in the hypo tube may define one or more tendons configured to actuate the beak(s). The cuts in the hypo tube may also define one or more tendon actuation tabs or body portion actuation tabs that enable actuation (e.g., opening and closing) the beak(s) through the tendons or body portion, according to embodiments, and limit the travel thereof. The tendon actuator tab(s) or body portion tab(s) may be located at any location along the length of the hypo tube. According to one embodiment, portions of the tube may be rigid. According to another embodiment, laser cuts along the proximally extended body portion of the tube may enable flexibility over its entire length or one or more portions thereof. The device may also comprise materials other than stainless steel, such as plastics or other suitable materials, which may incorporate the features of the beak(s), tendon(s), and, according to embodiments, tendon actuation tab(s) or an internal tube actuator element. This device may be used by itself or may be used in conjunction with or inside another excisional device with an open central lumen, through which it may introduced to attack a target tissue site.

FIG. 1 shows an excisional device 10 according to embodiments, having a tubular coring and transport assembly 11 (also called an "outer tube," "non- or differentially-rotating outer sheath," "flexible sheath" or "outer sheath" herein, depending on embodiments) of appropriate dimensions to retrieve a single or multiple morcellated or elongated core samples of tissue (not shown) that is or are sufficient to provide the desired clinical diagnostic or therapeutic result. Such an appropriate dimension may be, for example, about 6-40 inches in length, in addition to a forward excursion of a tubular coring and transport assembly 11 during the morcellating/pulsing/coring phases. It is to be understood, however, that the foregoing dimensions and any dimensions referred to herein are exemplary in nature only and are not limiting factors. Those of skill in this art will recognize that other dimensions and/or configurations may be implemented, depending upon the application, and that a tubular coring assembly and its subparts could be of any length.

One embodiment of the excisional device 10, as shown in the figures, may be implemented in a hand-held configuration comprising an ergonomically comfortable and secure handle 12 at its proximal end from which a tubular coring and transport assembly 11 extends so that the device 10 may be easily directed with one hand while the other hand is free to hold a guiding probe such as an ultrasound transducer. However, it is to be understood that embodiments may readily be configured to fit onto any number of guiding devices such as a stereotactic imaging stage or other guidance modality such as MRI (not shown). As shown, one embodiment of the device 10 may comprise one or more sharp, rotating cutting elements 13 (herein, alternatively and collectively referred to as "work element", "beak", "beak assembly" or "beak element" or "beak elements") projecting forward distally from the distal free end of the tubular coring and transport assembly 11 for the purpose of forward penetration, morcellation, coring and parting off of a cored sample in a simple point and shoot procedure. A tubular coring and transport assembly 11 may comprise a plurality of components, which plurality may be configured to transmit rotational movement to rotating cutting elements 13, as well as short excursion forward pulsed movement in a puncturing or "jackhammer" motion. It is to be understood that the "tubular" description of a coring and transport assembly may be of any cross-section shape and size, of any length. The components of a tubular coring and transport assembly 11 also transfer collected tissues and fluids back proximally along the internal length of an inner lumen of a tubular coring and transport assembly 11 to a handle 12 and storage compartment or a transfer magazine 27. According to one embodiment thereof, the device 10 may comprise a handle or handle 12, which handle or handle 12 may comprise and/or be coupled to mechanical components (not shown in this figure) needed to drive a morcellation/pulsed puncturing/coring/transport/part-off/delivery distal tubular coring and transport assembly 11. As shown, one embodiment may comprise a distally-disposed beak 13 that may comprise one or more sharp cutting tip blades to penetrate to the target site of the intended biopsy or intervention, morcellate and core the target tissue and part-off or cut off a hard or soft tissue sample (not shown) at its base or at any desired point along the length of a core sampling. The ability of the present device to repeatedly puncture, morcellate, core and retrieve multiple samples (not shown) during a single insertion and then store the cored samples in a transfer magazine 27 or other storage container means that with a single penetration through the skin of, for example, the thigh and femoral artery, the operator can sample multiple areas without causing additional trauma that would be associated with having to remove the device 10 each time a sample is taken, and reintroducing the device 10 back into the patient to take additional morcellated or cored samples. A handle 12 may also contain and/or be coupled to (internal or external) mechanical components (not shown) for vacuum-assisted fluid evacuation as well as the delivery of materials such as, for example, a variety of flushes, medications, tracer materials and/or implantable marker elements (not shown). A distal tubular coring and transport assembly 11, according to one embodiment, may be configured such as to create the smallest possible caliber (e.g., diameter) of coring tube (tubular coring and transport assembly 11) with a range of (for example) about 16 gauge or 0.065 inches in diameter to about 1 inch or more diameter, while providing a sufficiently large diameter of core sample to be clinically useful. A tubular coring and transport assembly 11 may also be constructed of flexible materials and/or of a sufficient length to reach distant target sites from the skin surface without the need for a surgical procedure to enable the distal end (that end thereof that is furthest from a handle 12) of the device 10 to reach the targeted site. In the embodiment of FIG. 1, a distal tubular coring and transport assembly 11 of the device 10 may extend distally from a handle 12 to a distance sufficient to create a tissue core (not shown) for diagnosis and/or treatment purposes. As is described below, this distance of forward or distal projection can be selectively changed at will, thanks to structure configured for that purpose, which may be built into or otherwise coupled to the present device 10. Embodiments of the present device 10 may be used by right and/or left-handed persons and in multiple positions and orientations so that in areas of limited access the present device may still be easily positioned for ideal orientation to perform an excisional procedure under real time or other image guidance (not shown). The entire device may be configured to be disposable or may be configured to be reusable in whole or in part. Embodiments of the present device 10 may be electrically powered by one or more batteries (not shown in this figure) and/or external power sources (not shown in this figure) through a simple electrical coupling to connect to an external power supply conveniently placed, for example, in a handle or proximal end of the present device. The entire device may also be internally or externally manually powered, mechanically powered or be powered by means such as compressed air, gas or pressurized fluid. Powering the device entirely mechanically may be advantageous in areas in which the electric grid is absent, unavailable, or unreliable.

FIGS. 2 and 3 show details of components of a work element, according to one embodiment. Attention is drawn to the proximal end of a work element 13. Therein, a body portion 428 of a work element 13 may be mechanically coupled to tendon actuating element 469 at the proximal end of a work element. Note that a tendon actuating element 469 is already coupled to a body portion 428 through tendons 468, 470, toward the distal end of a work element 13. That is, an entire work element 13 may be formed of a single homogeneous material—such as from a single hollow tube that is (for example) laser-cut to form the structures shown in FIGS. 2 and 3. Two beaks are shown. It is to be understood, however, that such need not be the case, as a work element 13 may comprise multiple beaks or a single beak that acts against a non-moveable part, such as a fixed trough-shaped distal portion of a distal sheath or against a fixed, opposing beak that is part of a work element 13 itself.

According to one embodiment, as shown in FIGS. 2 and 3, the proximal end of a tendon actuating element 469 may be mechanically coupled to the proximal portion of a body portion 428. Such mechanical coupling may be configured to maintain a tendon actuating element centered on the cutout in a body portion formed to accommodate a tendon actuating element 469 and/or to provide additional biasing force in the distal direction, as well as to aid in manufacturing. One embodiment comprises a resilient member 427 having one end thereof coupled to a tendon actuating element 469 and another end thereof coupled to a proximal portion of the work element 13. Such a resilient member 427 may be configured to bias the beak or beaks of a work element 13 in the open configuration, such that a sufficiently great proximally-directed force applied to a tendon actuating element 469 tends to close a beak or beaks. Conversely, release of such proximally-directed force causes a resilient member 427 to release the energy stored during the extension thereof and return to its un-extended state, thereby exerting a distally-directed force on a tendon actuating member 469, which causes a beak or beaks to return to its or their default open configuration.

Also shown in FIG. 3, attachment holes 292A and 292B may be provided on a body portion 428 and on a tendon actuating element 469, respectively. Such attachment holes 292 may, according to one embodiment, indicate the location of, for example, spot welds, as detailed below.

Figure 4:
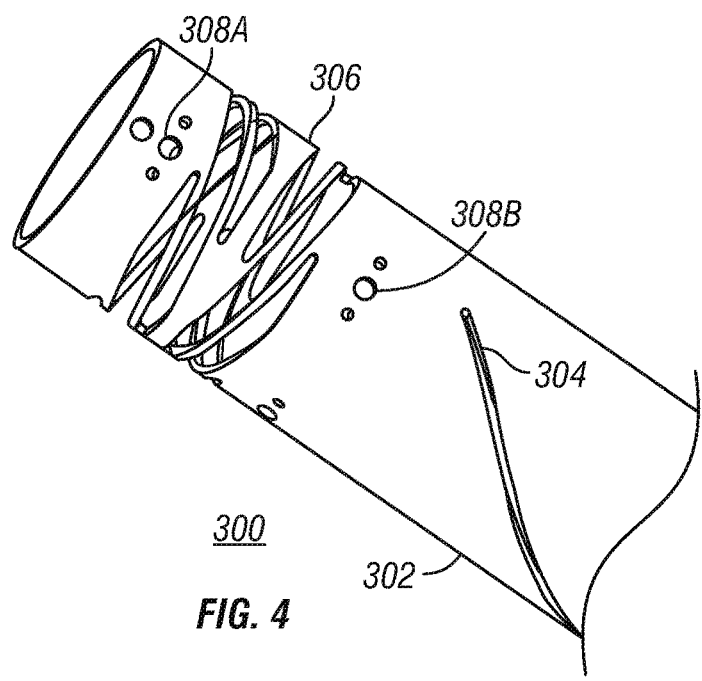
FIG. 4 shows the distal end of a proximal sheath of an excisional device according to one embodiment.
Figure 5:
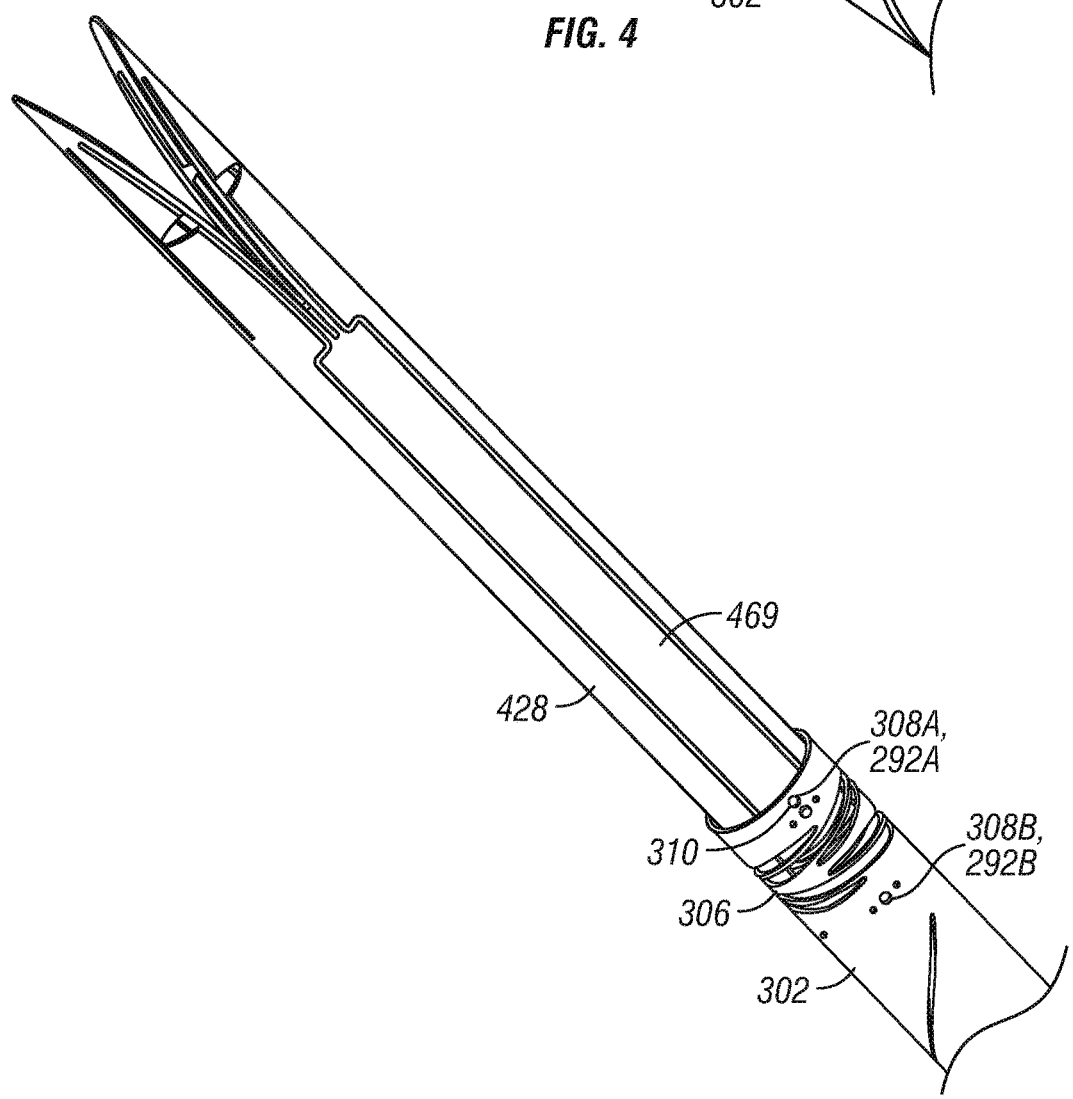
FIG. 5 shows an assembly comprising a monolithic beak assembly and a proximal sheath of an excisional device according to one embodiment.

FIG. 4 shows a distal portion of a proximal sheath according to one embodiment. A proximal sheath 300, as shown in FIG. 4 may comprise a number of fenestrations or slots 304 that run through the wall of a proximal sheath 300, from an outer surface to an interior lumen thereof. The distal portion of a proximal sheath 300 may be configured to fit over and attach to the proximal end of a monolithic beak assembly 13 of FIGS. 2 and 3. During assembly of the present excisional device and as shown in FIG. 5, attachment holes 308A and 308B of a proximal sheath 300 may be lined up with attachment holes 292A and 292B, respectively, of a monolithic beak assembly 13, as illustrated in FIGS. 2 and 3. A proximal sheath 300, which may be flexible along its length, may thus be attached to a monolithic beak assembly 13 at attachment points 292A, 308A and 292B, 308B. According to one implementation, an attachment point 308A of a proximal sheath 300 may be spot-welded to an attachment point 292A of a tendon actuating member 469 of a monolithic beak assembly 13. Although not shown in these figures, corresponding attachment points may be provided on the hidden side of the device. Similarly, an attachment point 308B of a proximal sheath 300 may be spot-welded to an attachment point 292B of a body portion 428 of a monolithic beak assembly 13. As also shown in FIG. 4, the distal portion of a proximal sheath 300 may define a resilient or spring portion, as shown at reference numeral 306.

Figure 6:
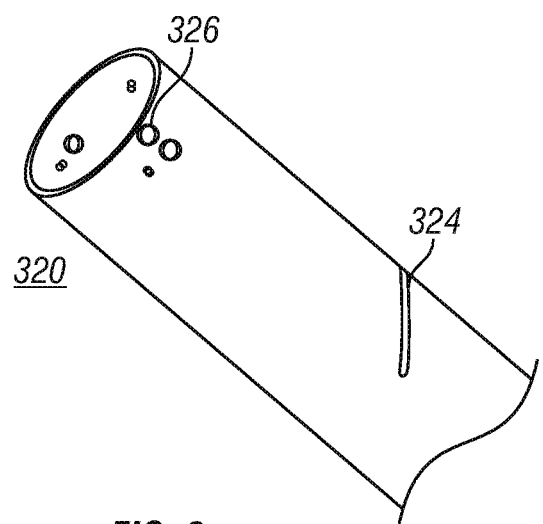
FIG. 6 shows the distal end of a distal sheath of an excisional device, according to one embodiment.
Figure 7:
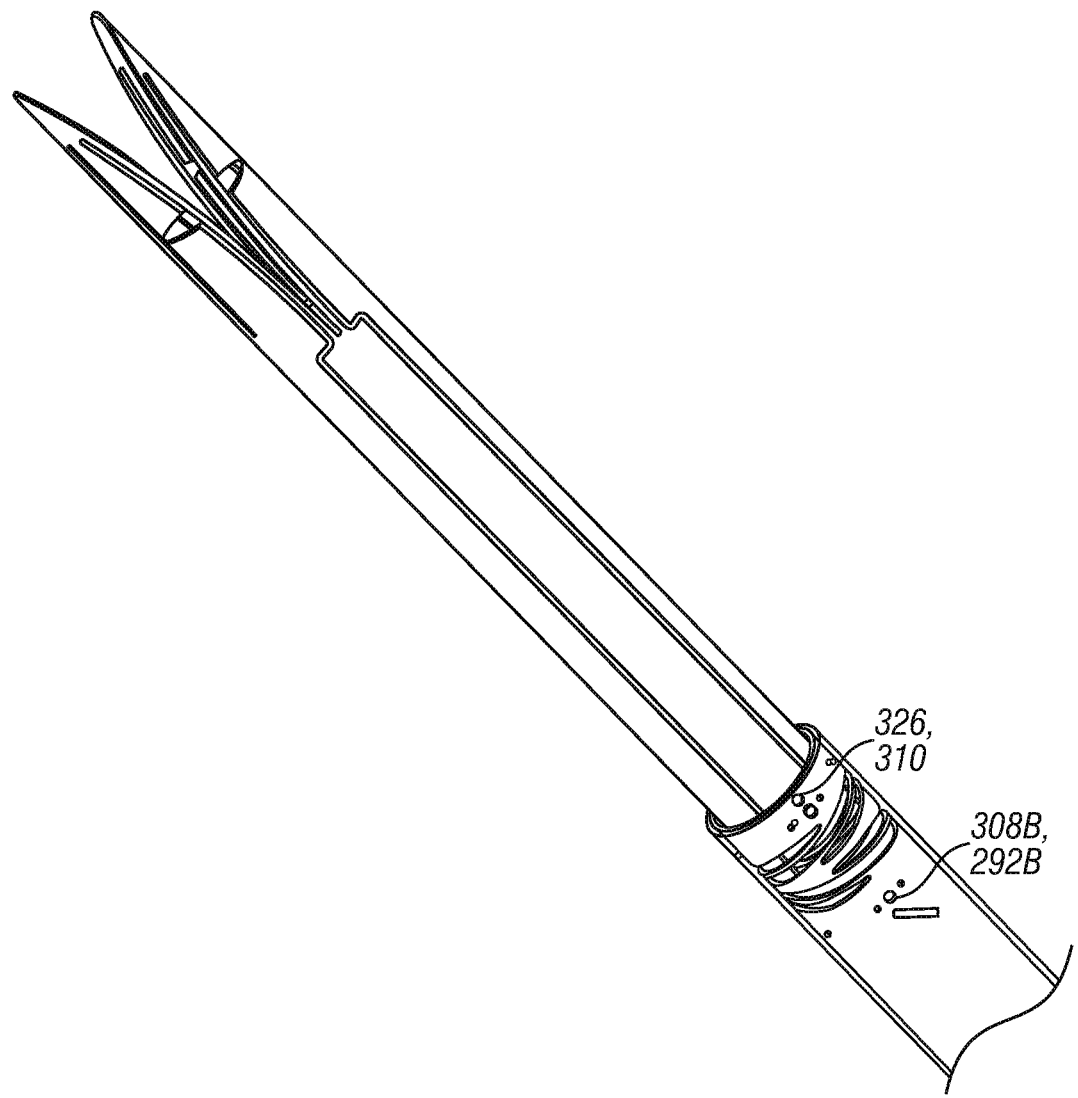
FIG. 7 shows an assembly comprising a monolithic beak assembly, a proximal sheath and a distal sheath, according to one embodiment.

FIG. 6 shows the distal portion of a distal sheath 320, according to one embodiment. A distal sheath 320, which may also be flexible along its length, may be configured to fit over a proximal sheath 300 and an attachment point 326 of a distal sheath 320 attached to attachment point 310 on a proximal sheath 300, as shown in FIGS. 5 and 7. For example, an attachment point 326 of a distal sheath 320 may be spot-welded to attachment point 310 on a proximal sheath 300, as suggested in FIG. 7. A distal sheath 320 is transparently illustrated in FIG. 7, to show underlying detail. It is to be understood that spot-welding is but one method of attaching constituent components of the present excisional device to one another. Other attachment technologies may also be used, as appropriate. Once a distal sheath 320 is spot welded in place, it will rotate in synchronicity with a beak assembly 13 and proximal sheath 300, but will be able to move axially relative to proximal sheath 300, according to one embodiment. Such axial movement between distal and proximal sheaths will positively open and/or close a beak or beaks of monolithic beak assembly 13, as previously discussed. As will be discussed further below, such a structure may also incorporate collar elements, in which case the attachment points of the distal sheath to such collar elements and at least one of the collar elements to the beak assembly 13, according to other embodiments. It should be noted that, according to embodiments, the distal sheath 320 may extend distally beyond the attachment points 326 to at least partially cover the monolithic beak assembly of FIGS. 2, 3 and 5, and may extend nearly to the beak tips, according to one embodiment.

Figure 8:
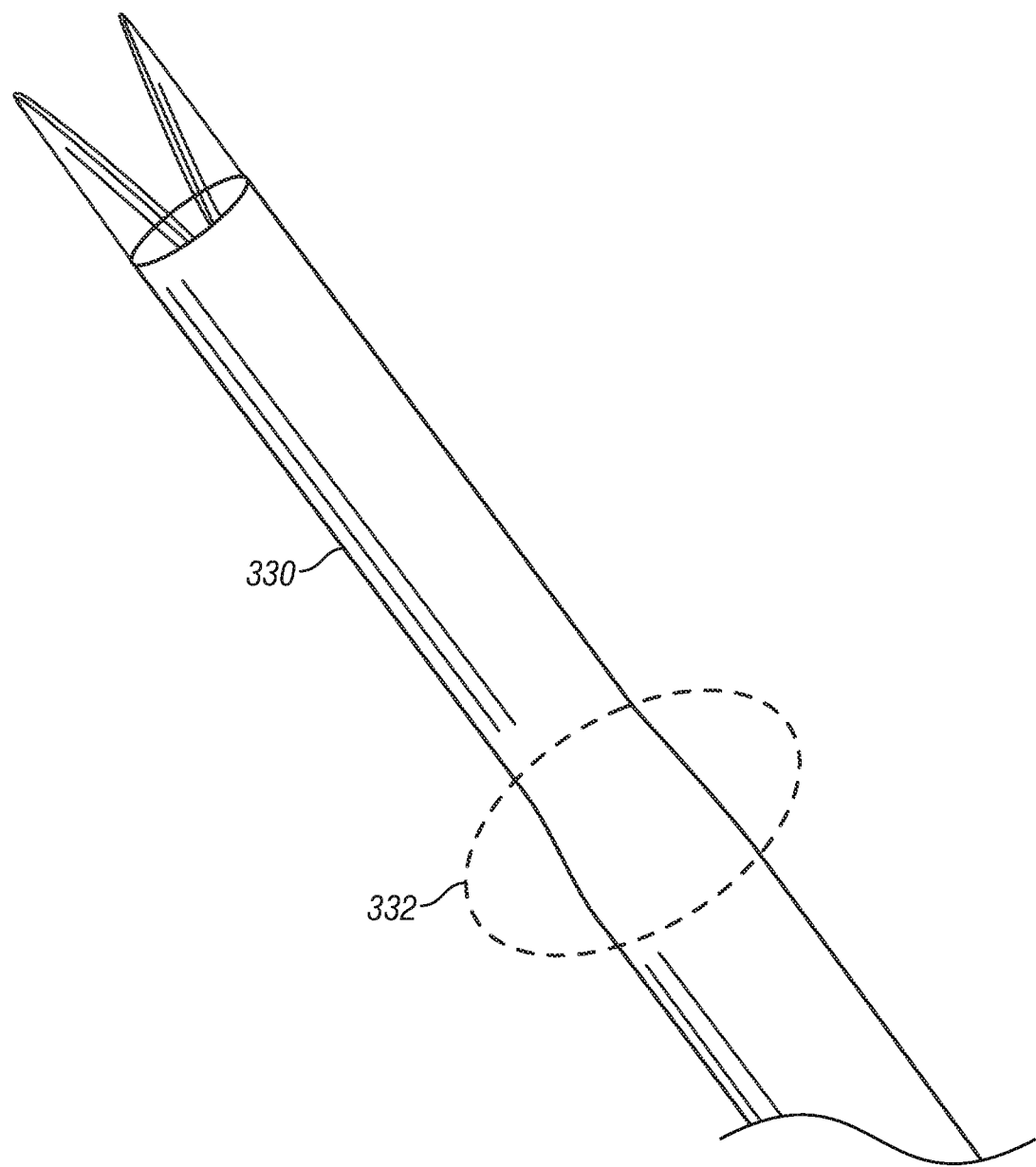
FIG. 8 shows the distal portion of an excisional device according to one embodiment.

FIG. 8 shows one embodiment of the present excisional device, in a still further intermediate state of assembly. In FIG. 8, an outer sheath 330 has been fitted over an assembly comprising a monolithic beak assembly 13, a proximal sheath 300 and a distal sheath 320, according to one embodiment, or over an assembly comprising a monolithic beak assembly 13, a proximal sheath 300 and a simple collar, according to another embodiment. For example, an outer sheath 330 may comprise polyimide or may comprise or be formed of stainless steel among other suitable materials. An outer sheath 330 may be configured to be manually rotating, non-rotating, or at least differentially-rotating with respect to an assembly comprising a monolithic beak assembly 13, a proximal sheath 300 and a distal sheath 320 and may further be configured to be removable. That is, in this embodiment, while an assembly comprising a monolithic beak assembly 13, a proximal sheath 300 and a distal sheath 320, if included according to embodiments, may rotate at relatively high rates of speed (in the thousands of revolutions per minute, for example), an outer sheath 330 may be held either stationary or rotated as needed. This may be accomplished manually or otherwise actuated by any mechanical means. For example, the user may rotate an outer sheath 330 a few tens of degrees at a time, as and when the procedure requires, and may remove or replace it before, during or after a procedure. An outer sheath 330 may extend distally to beaks of a monolithic beak assembly, may expose a greater proportion of a monolithic beak assembly 13 or may cover a significant portion of beaks, which may be controlled during use, according to embodiments. Different distal shapes at the end of the outer sheath 330 may be incorporated, according to further embodiments, and may include scoop-shaped or castellated configurations.

According to one embodiment, an outer sheath 330 may be dimensioned so as to allow an annular space to exist between the inner wall of an outer sheath 330 and the combined outer surfaces of a distal sheath 320 and distal portion of a monolithic beak assembly 13. This annular space may allow for flush to be introduced at selected stages in the procedure. The flush may provide lubrication for the rotation of an assembly comprising an assembled monolithic beak assembly 13, a proximal sheath 300 and a distal sheath 320, and may facilitate the rotation and thus the transport of the cored and severed tissue specimen in the distal direction. According to one embodiment, when the beak or beaks of a monolithic beak assembly is or are in the open configuration, fenestrations or slots 304 (FIG. 4) defined in a proximal sheath 300 are not lined up with fenestrations or slots 324 (FIG. 6) defined in a distal sheath 320. However, according to one embodiment, when beak or beaks are actuated, and beaks are closing, are closed or are substantially closed, then fenestrations or slots 324 defined in a distal sheath 320 become lined up (or substantially lined up) with corresponding fenestrations or slots 304 defined in a proximal sheath 300. In this state, if there is flush in an annular space between the outer surface of a distal sheath 320 and the inner wall of an outer sheath 330, this flush will enter the interior lumen of the device (where the cored and severed tissue specimens are collected and are transported). Moreover, as the flush may have been entrained into rotation in an aforementioned annular space as the assembly comprising a monolithic beak assembly 13, a proximal sheath 300 and a distal sheath 320 rotates, the rotating flush may enter this interior lumen with some force and may exert that force on any cored and severed tissue specimen therein. This flush may act as a lubricant as well to the specimen contained in the inner lumen of the device. According to one embodiment, a vacuum may be drawn within the interior lumen of the device. According to one embodiment, the vacuum force imparted on the cored and severed tissue specimen, alone or together with force imparted on such specimen by flush entering this interior lumen, draws and transports the cored and severed tissue specimen in the proximal direction, for eventual transport to a transfer magazine 27, for example.

Transport of cored tissue specimens may be aided by a shoulder shown at 332 in FIG. 8. Indeed, such shoulder encompasses the location defined by the proximal end of a monolithic beak assembly 13 and the distal end of a proximal sheath 300 as well as the distal end of a distal sheath 520 or a simple collar attached to the beak assembly. As the diameter of a proximal sheath 300 is somewhat greater than that of the proximal end of a monolithic beak assembly 13, the interior lumen of a proximal sheath 300 is correspondingly larger than the interior lumen of a monolithic beak assembly 13, and the interior lumen of a proximal sheath thus serves as an expansion chamber or, according to embodiments, as a stop barrier for a collar to act against under rotation or not. As the cored and severed tissue specimen(s) enters the interior lumen of a monolithic beak assembly 13, the tissue specimen(s) may be somewhat compressed. Such compression may be somewhat relieved as the tissue specimen(s) transitions from the lumen of a monolithic beak assembly 13 to the somewhat greater diameter lumen of a proximal sheath 300, at shoulder 332. This decompression of the tissue specimen(s) in the lumen of a proximal sheath 300 may, together with flush and/or vacuum, also facilitate tissue transport. A shoulder at 332 could expand an inner lumen diameter in the range of 0.001 inch to 0.100 inch additional over an original lumen diameter, or double a lumen diameter, whichever is greater. As previously mentioned, shoulder features may be incorporated into a proximal sheath, distal sheath and outer sheath to augment such tissue expansion/transport action. As previously mentioned may be the case, such an embodiment may or may not incorporate a first helical element (transport helix which may be in the form of an Archimedes screw) or may instead be constituted of co-axially disposed helices, for example, in the form of a proximal sheath and a distal sheath, which, aided by flush and/or vacuum, may efficiently transport tissue specimens axially to a transfer magazine at the proximal end of the device 10.

According to one embodiment, flush may be incorporated in the annular space between an outer sheath (which may actually take the form of either a distal sheath 590 or an outer sheath) and inner sheath(s), to facilitate tissue transport. Vacuum may be drawn within the central lumen of a whole tubular coring and transport assembly 11, to facilitate tissue transport as well as flush fluid transport. This enables an operator to collect any fluids from the penetration and biopsy or intervention sites during the procedure in order to help with visualization under various guidance modalities and to collect cells for cytological analysis. Moreover, according to one embodiment, such a flush pathway enables the delivery of, for example, biologically active substances and/or markers.

Coupled with flush and vacuum, fenestrations defined in a proximal sheath and a distal sheath may enable a helical "pumping" feature and create a reservoir of fluids surrounding the tissue, which may enable a swirling wave action to interact with the cored and severed tissue samples to gently push them in the proximal direction. Such fenestrations may also lessen respective wall surface areas of these structures and thus decrease the surface friction experienced by the cored and severed tissue sample. Such structures also exhibit a favorable "sealing" effect surrounding the tissues, particularly where irregular tissues might, based on their own surface architecture, engender vacuum leaks. Indeed, the gentle urging of such transportation of the cored and severed tissue samples preserves the underlying tissue architecture and delivers a clinically-useful sample (e.g., one whose tissue architecture has not been unacceptably damaged during its transport) to, for example, a transfer magazine 27.

Figure 9A:
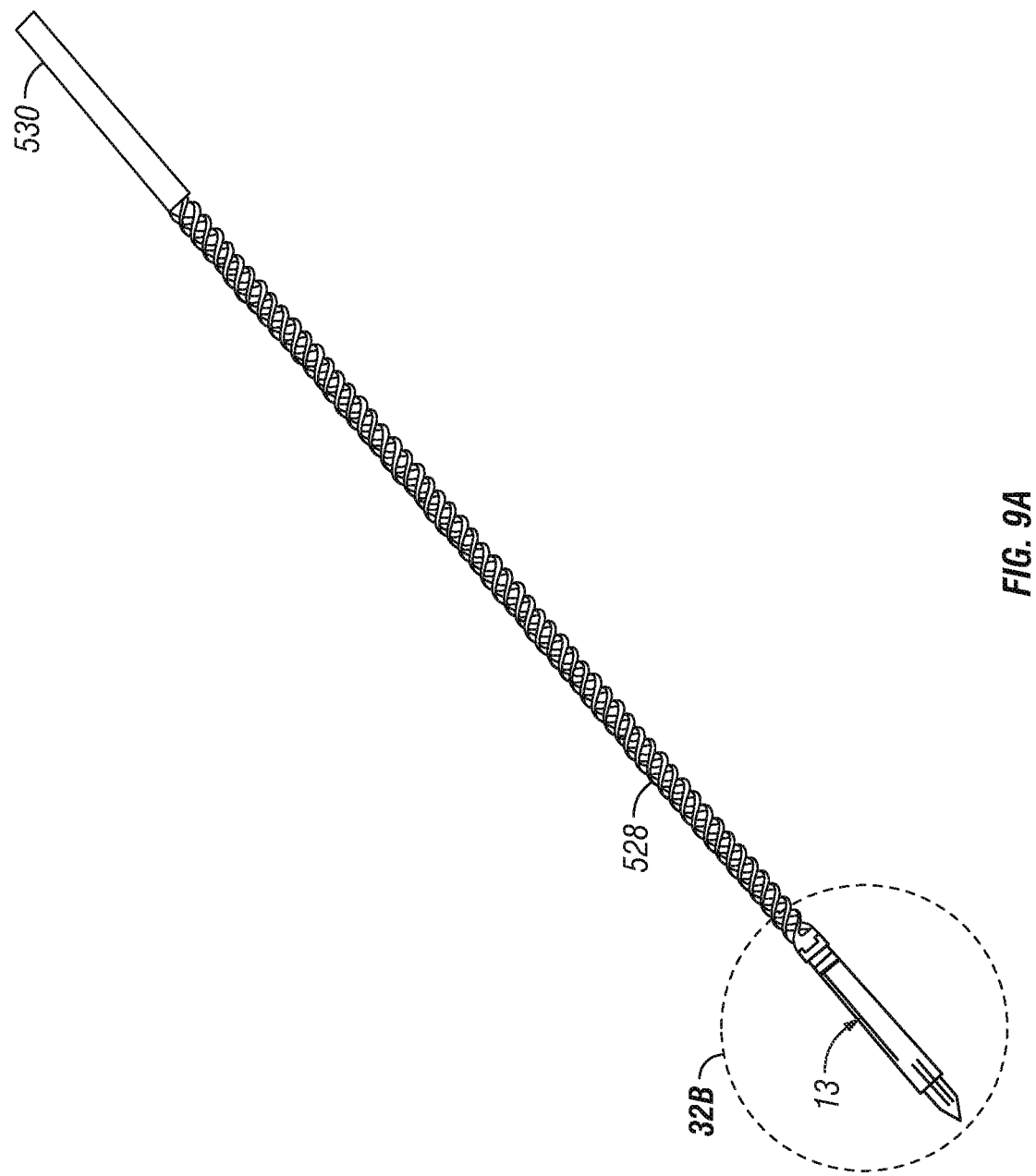
FIGS. 9A and 9B illustrate details of a collar actuation mechanism of a work element of a device, according to one embodiment.
Figure 9B:
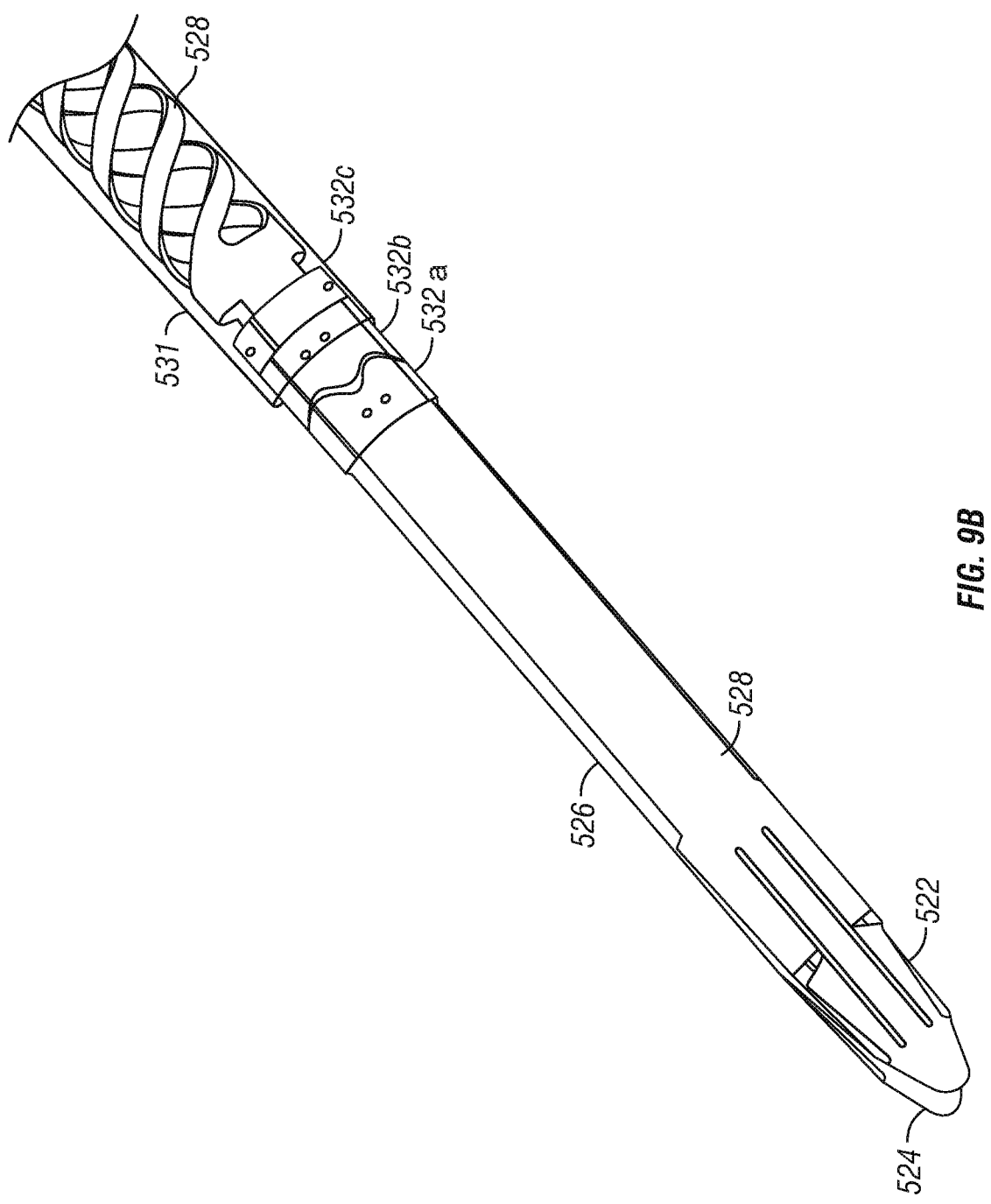

FIGS. 9A and 9B illustrate details of a collar 532 actuation mechanism of a monolithic work element of a device according to one embodiment. Such a collar may be attached to a tendon actuation tab 526, as well as a body portion 528 of a work element, and provides for differential axial movement of a tendon 522, for example, in relation to a body portion 528 of a work element 13, thus allowing for beak actuation. In this figure, a collar 532 may be comprised of three sub-elements, 532a, 532b and 532c, the most distal of which (532a) may be attached to, for example, a body portion 528 of a work element, the middle collar (532b) attached to a co-axially placed outer tube 531, and the most proximal collar (532c) attached to the tendon actuation tab 526. If the outer tube is rotated in relation to the work element, the sinusoidal or other form of wave around the periphery of the adjacent-most distal collar and middle collar will provide relative axial motion between the body portion 528 of the work element and the tendon actuation tab 526 of the work element, thus actuating the beak tip(s) without allowing the beak tips to twist in relation to one another. Such a configuration may be advantageous in allowing for beak actuation wherein the proximally extended body portion 530 of the inner monolithic work element tube may be, for example, over 3 feet in length and flexible over its length as may commonly be associated with vascular intervention devices. An outer tube 531, which may also be flexible in construction (such as shown in FIG. 9A by the helical structure, but with an opposite twist, for example), would therefore still efficiently translate rotation along its entire length in relation to the inner work element flexible body portion, allowing efficient remote actuation of the work element at its distal end. It should also be noted that if the outer tube 531 is pulled axially in a proximal direction while the work element 13 is stationary, then the middle collar 532b will pull the proximal collar 532c in a proximal direction as well, resulting in the beaks closing. Similarly, if the body portion 528 is pushed distally while the outer tube 531 is stationary, the beaks will also close. Such a configuration allows the beaks to be actuated either as a result of differential rotation of the body portion 528 and outer tube 531, or by relative axial motion between those two structures. Finally, it should be noted that outer tube 531 may extend distally beyond its connection or weld points to the middle collar 532b such that it may cover the beaks 524 nearly to their very tips for efficient tissue coring purposes, according to embodiments.

Such a configuration of the three collar sub-elements may also be applied to the work element of FIGS. 4 through 7 above, in which case the distal most collar, 532a may be attached to the body portion 428 of the work element, collar 532b may be attached to the distal tube 320 of FIG. 6, and the proximal tube 302 of those illustrations may take the place of collar element 532c, for example, and according to another embodiment. In this embodiment, the proximal tube 300/302 is attached to the base of the work element along the body portion 428 by weld points 308B and 292B, and the flexible portion 306 of the proximal tube and the distal most extension of that tube would butt up against the collar 532b and is of the same diameter as the collar elements 532a and 532b. The middle collar 532b is attached to the distal tube 320 at weld points 326 and 310 of FIG. 7, extending forward of the distal end of proximal tube 300/302 of FIG. 5, and the distal-most collar 532a would be attached to the body portion 428 of the work element distal to collar 532b; would be the same diameter as collar 532b and the distal end of the proximal tube 300; and would thus serve as a hard stop against which any relative rotational motion between the proximal and distal sheaths 300 and 320, respectively, will serve to actuate the beaks of the work element by acting on the tendon actuation member 469 as the sinusoidal or other form of a wave or waves of elements 532a and 532b of FIG. 9b are rotated against each other. In such embodiments as those in this paragraph and the previous FIG. 9B, the proximal and distal tubes need not rotate in synchronicity, but may rotate in relative rotational speeds. Such a relative rotational motion enables a periodic flexing of the beaks of the work element, which may result in the beaks being closed completely, partially, or in any combination of such motion, depending only upon the profile of the peaks and valleys (waveform) defined by the facing peripheral surfaces of the collars 532a and 532b of FIG. 9B, as adapted to the work element of FIGS. 5 and 7 above and as described herein. For example, the wave form of elements 532a and 532b may include two shallow sinusoidal waves followed by one deeper wave form around the circumferences of the collar elements, and relative rotational motion of the proximal and distal sheaths would thus produce two partial beak closures and one full beak closure for one complete relative rotation between the proximal and distal sheaths. As an example of relative rotational speeds between the proximal and distal tubes, the proximal tube may be rotated at 10,000 RPM while the distal tube may be rotated at 9,940 RPM and thus lag the rotational speed of the proximal tube or vice versa with a rotational speed of 10,040 RPM, according to embodiments. Such differential rotational speeds may result in one full relative rotation of the distal and proximal sheaths each second, or 60 times per minute, for example. Other relative or absolute rotational speeds may be induced by the driving assembly of the device 10, according to embodiments and methods.

It is also important to note that in this embodiment related to FIGS. 5 and 7, as well as for the embodiment previously described in FIG. 9B above, that work element beak closure may also be manually induced by simply pulling the distal sheath 320 axially in a proximal direction in relation to the proximal sheath 300/302, or pushing the proximal sheath 300/302 in a distal direction, which may allow an operator to selectively close the beaks from the handle 12 end of the device 10 in the absence of any relative rotational motion and beak morcellation action induced between the proximal and distal sheaths, or in concert with such motion. Furthermore, in this embodiment as well as that described for FIG. 9B above, pushing the distal sheath 320 distally in axial motion would therefore not actuate the beaks, as the distal sheath would only push collars 532a and 532b axially together. As a result, any periodic axial motion induced onto the distal sheath 320 would result in the beaks of the work element, in any position (open position, closed or partially closed) to move the entire work element distally and proximally by a defined distance, according to further embodiments and methods. Such axial motion of the distal sheath therefore is independent of any induced axial motion of the proximal sheath, and thus allows the driving mechanism to induce a full range of motions of the work element, as desired by the operator, including a simple coring under rotation, a jackhammer or puncturing motion of the beaks with the beaks in any position, a pulsed or periodic morcellation action of the beaks, partially or fully closing and opening, or in any combination of those motions with the additional option of being able to close the beaks manually at any time. An embodiment of a simple driving mechanism to enable such motions is described further herein in later sections.

Figure 10A:
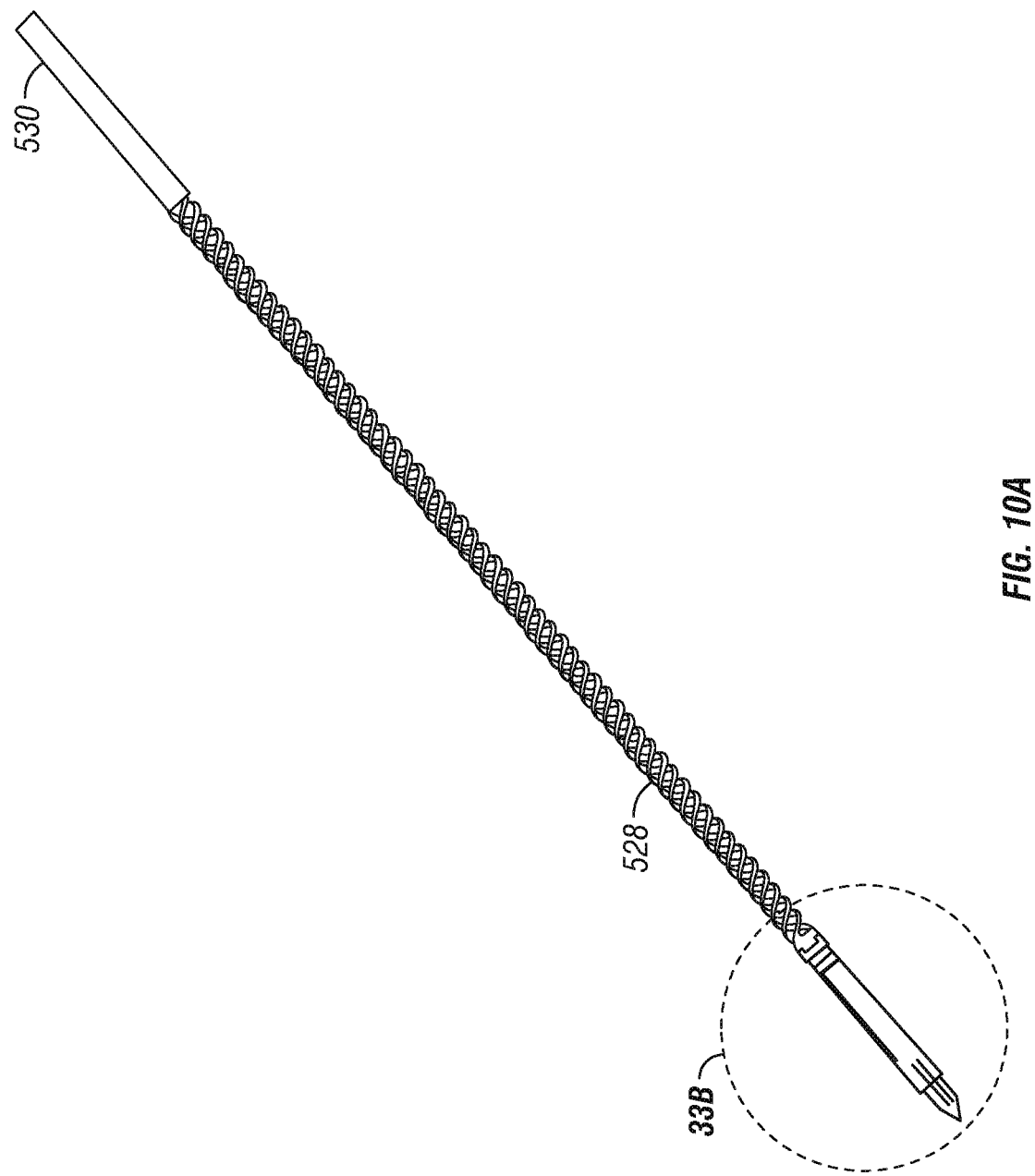
FIGS. 10A and 10B show elements and features of a single flexible tube work element with double articulable beaks or scoopulas, according to embodiments.
Figure 10B:
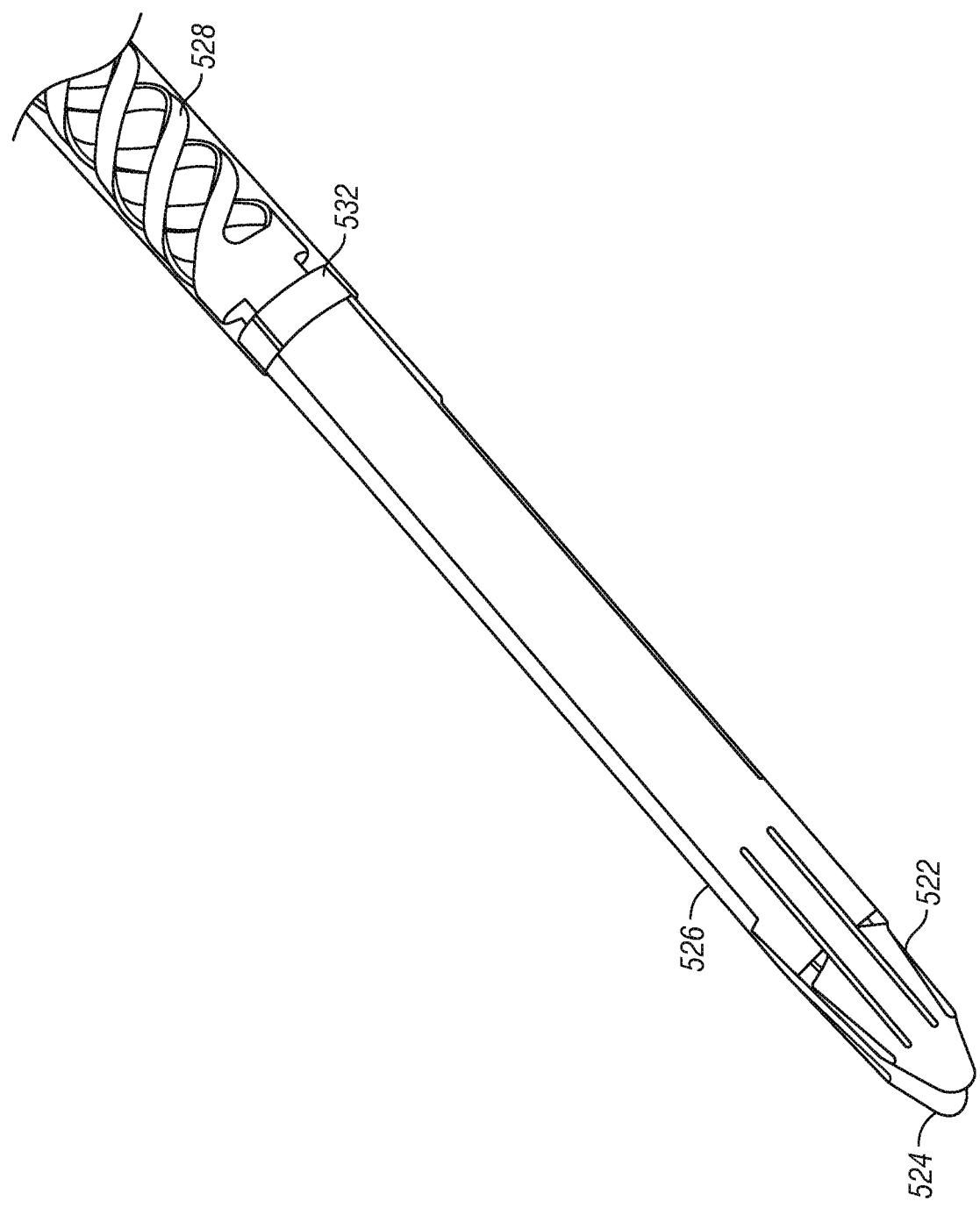

FIGS. 10A and 10B show features and elements of a single monolithic tube 530 of a work element, which may comprise at its distal terminus one or more fixed or articulable beaks, according to various embodiments. In one embodiment, a work element is comprised of a single tube 530, which may have a flexible portion 528 or portions disposed along its axial length. In FIG. 10B, details of the distal end of a work element may be seen, with beak tip(s) 524, tendon(s) 522, tendon actuation tab(s) 526, a collar element 532 fixed to the tendon actuation tab(s) 526, and a flexible tube portion 528, which may be coated to maintain liquids within its central lumen while remaining flexible. As shown, a proximally-directed force applied to collar 532 while maintaining the body portion 530 fixed would tend to close the beak(s) or scoopula(s) (cause them to flex towards the longitudinal axis of the work element). The outer tube 330 of FIG. 8 above, which may also be flexible along its length, with its shoulder 332 acting as an internal stop barrier to the collar 532 of FIG. 10B, would allow for pulsed axial motion of the beak tips, as induced by the driving assembly of the handle 12 of device 10, but in such an embodiment, such puncturing or jackhammer action would be accompanied by partial or complete simultaneous closing down of the beak elements, according to one embodiment.

Figure 11:
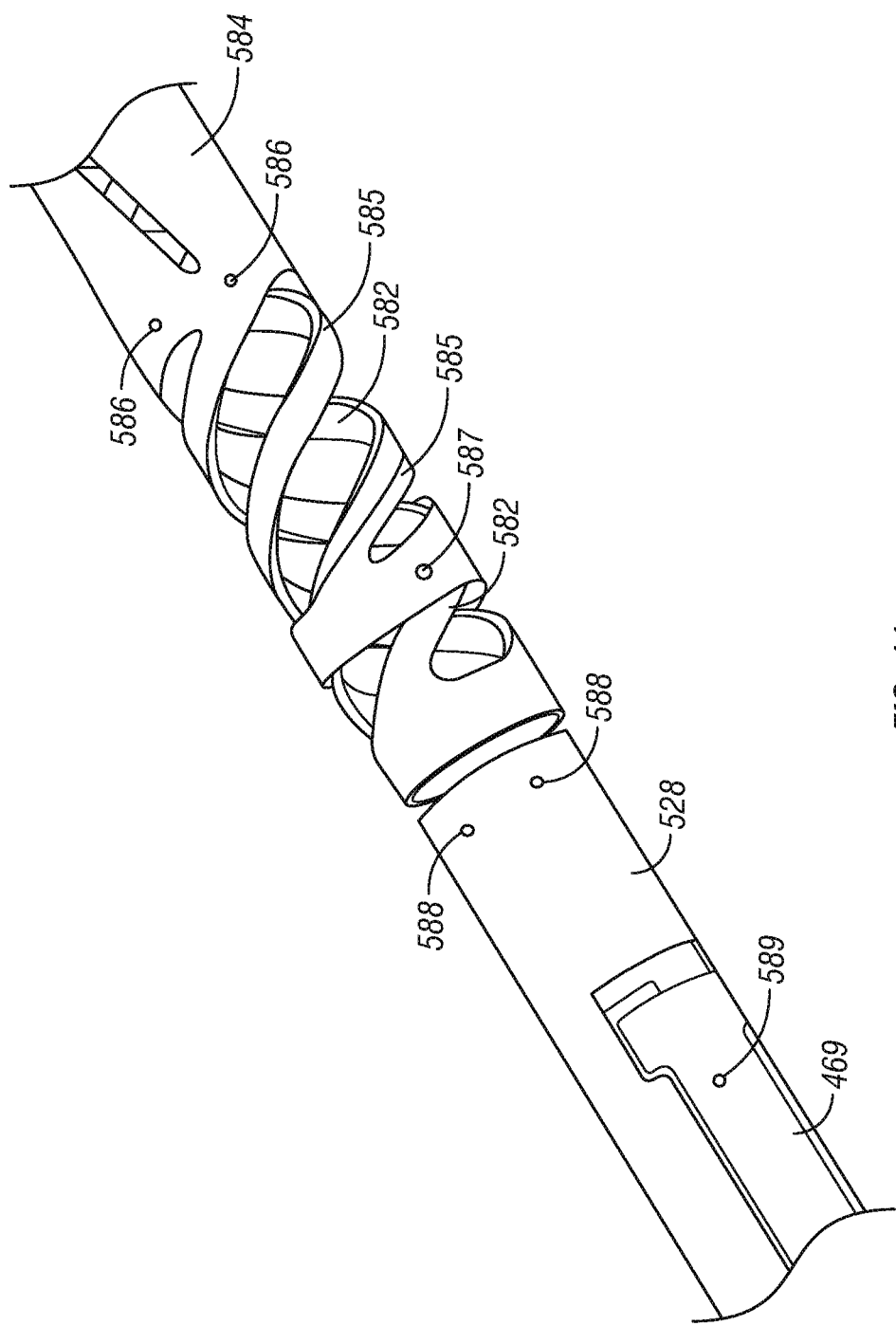
FIG. 11 shows elements of a double tube work element proximal end, according to one embodiment.

FIG. 11 is a side perspective view of elements of a work element, according to one embodiment. In this example, a tendon actuation tab 469 is present, similar to the distal end of the work element of FIG. 10A and similar to element 526 of FIG. 10B. The distal beak or beaks or scoopula or scoopulas are not visible in this illustration. In this illustration these structures are to the left, off the page, whereas the proximal end of the device 10 (comprising the handle 12 and other ancillary structures are to the right, off the page. In this embodiment, an inner tube and an outer tube are coupled to the work element. Elements of the inner tube comprise a tendon actuation tab 469, a tendon actuation tab welding point 589, a body portion 428, body portion welding points 588 and may also feature an extended flexible body portion 1b, which may be either contiguous with body portion 468, or separated as shown in the illustration, in which case it may take the form of an Archimedes screw, according to embodiments. The flexible helical or other shaped portion 582, may be coated according to one embodiment. An outer tube 584 may also feature a flexible element 585, a spot weld or glue hole 587 which may be matched to weld point 589 of an inner tube, and spot weld or glue holes 586 which may be matched to weld points 588 of an inner tube of a work element. An outer tube may also contain additional features for flexibility along its axial length or cuts such as 584 to enable vacuum or flush functions to be incorporated into a work elements overall function. An outer tube may also have an outer coating, according to one embodiment. Such an embodiment may also function with a flexible or rigid outermost tube 330 of FIG. 8 above which would enable beak actuation and pulsed puncturing motion of the work assembly of the device 10, as described above for FIG. 10B, but with the outer tube 584 distal end acting upon the shoulder element 332 of such an outermost coaxial tube.

Figure 12:
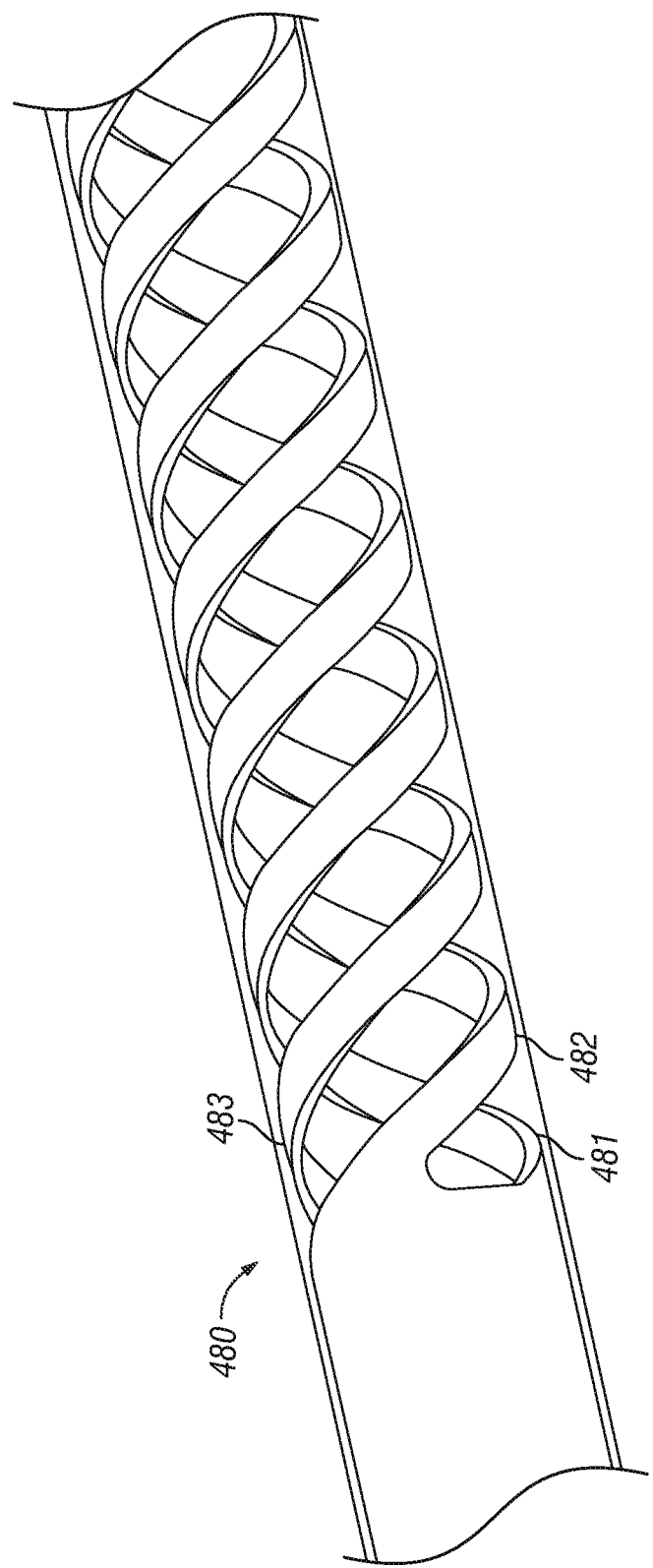
FIG. 12 shows a flexible, coated helical structure for a tube element of a work element, according to one embodiment.

FIG. 12 shows a configuration of a flexible body portion 480 of a work element 13 tube, according to one embodiment. Flexible elements 481 and 482 may be disposed along its length and it may also be coated along part of all of its axial length, as indicated in this illustration.

Figure 13:
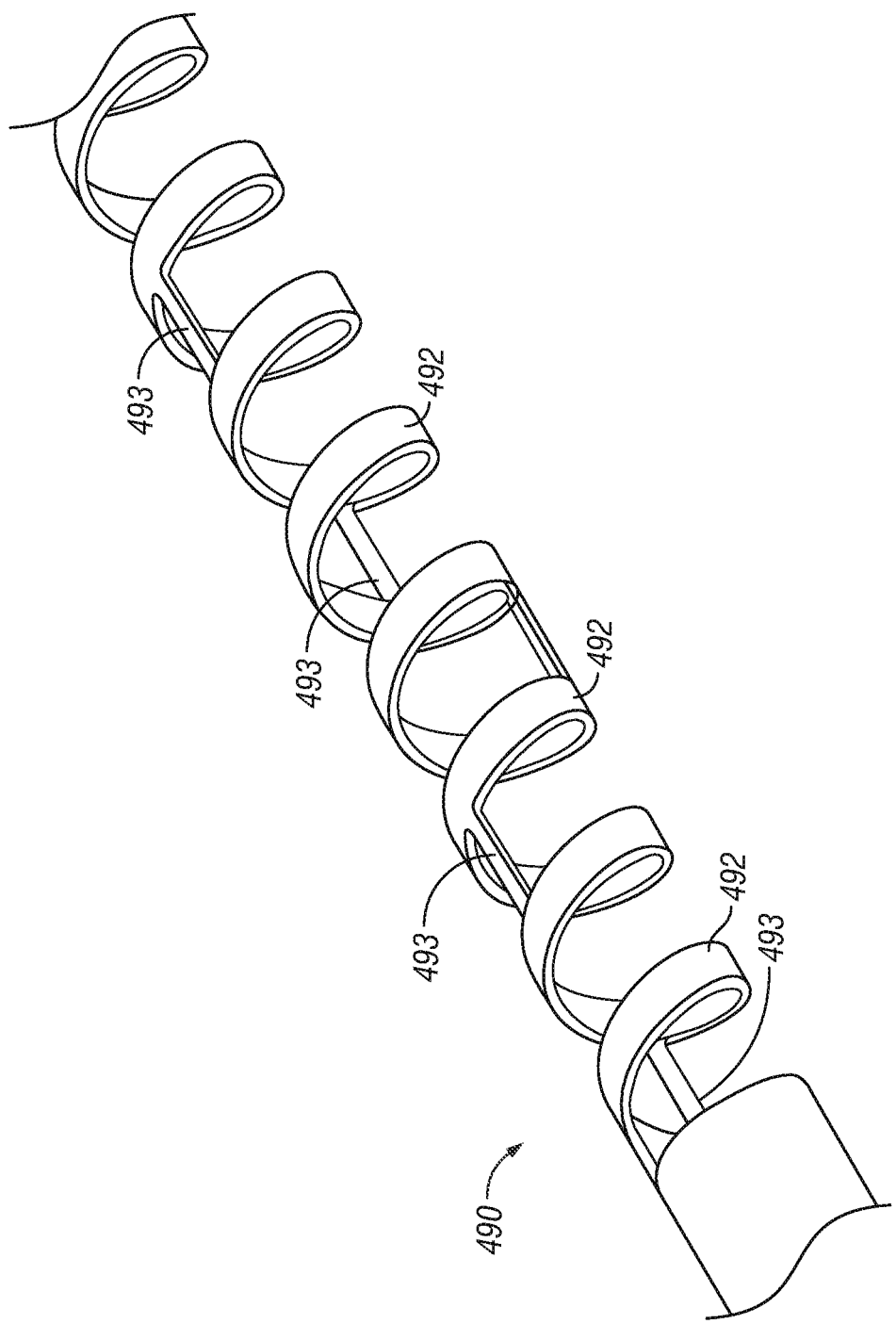
FIG. 13 shows a flexible, axially-constrained tube element of a work element, according to one embodiment.

FIG. 13 is one configuration of a flexible body portion 490 of a work element 13 tube, according to one embodiment. Flexible elements 492 may have one or more linking structures 493 incorporated, and may be formed of a single laser cut hypo-tube, for example. There may be one or more such linking structures 493 for each turn of such a helix structure, which may also join multiple helices such as found in FIG. 12 above, in which case each link would alternately attach one helix to the other. Such linkages may serve to stiffen axial compression characteristics of a tube while still allowing lateral flexibility. Other helical structures to allow a similar latitude of functions may be readily envisioned, and are considered within the scope of this disclosure. A body portion 490 of a work element tube may also be coated or uncoated along part of all of its axial length, according to embodiments.

Figure 14A:
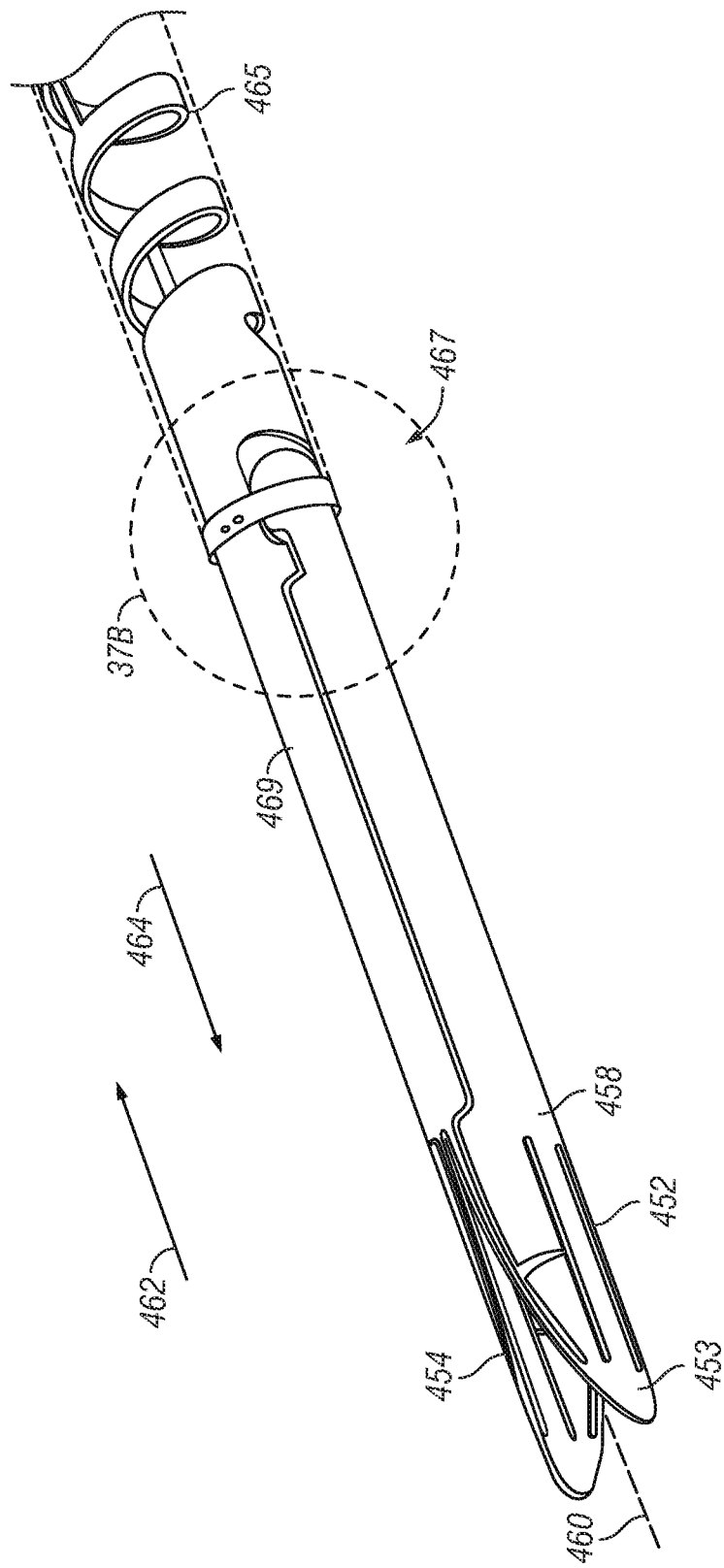

FIGS. 14A and 14B illustrate elements and features of a single tube work element, according to one embodiment. FIG. 14A shows a single tube with a distal work element as a monolithic structure and a proximal flexible extension 465 thereof. Reference numeral 460 illustrates a line of sight through the central lumen of the work element, which features one or more tip element(s) 453 (one of which may be fixed and non-articulable if two or more are present), living hinge(s) 452 formed by kerfs in the work element, tendon(s) 454, a tendon extension element 469 (as opposed to a tendon actuation tab discussed under other embodiments herein) and a body portion 458. Also illustrated is a collar 432, similar to that collar 532 of previous illustrations, which may be a simple collar or an outer tube serving the same purpose, as suggested by the dashed lines extending proximally. The actions suggested by arrows 462 and 464 represent the action of the work element with differential axial forces acting on the tendon extension element 469 and body portion 458 of a work element, according to this embodiment. If, for example, element 469 is held in place while a distally-directed force 464 is applied to the body portion extension 458, the distal tips of the work element will tend to close and the reverse will be true if a proximally directed force 462 is applied to the work element. If an outer tube, such as that illustrated in FIG. 8 above were to be placed over this single tube work element, the collar 432 could be actuated by periodic or sustained pressure against the internal shoulder 332 of the outer tube, which actuation could result in a combined simultaneous jackhammer-morcelation action of the beaks as they open and close-moving slightly forward during closing.

FIG. 14B shows expanded details of portion 467 of FIG. 14A, wherein the collar 532 (or rigid or flexible outer tube, according to other embodiments) is fixed to the tendon extension element 469 by spot welding, for example. Note that in this embodiment, the body portion extension tab element 458 is unconstrained and is free to move axially in either direction within the limits of the aperture from which it is formed in the work element. In this embodiment, one or more dimples 701 may be welded onto the body portion extension tab, and extend under the collar or tube 532, thus pushing the tab slightly into the central lumen of the work element, and allowing it to be abutted by and acted upon by a tube, for instance, that may be placed into the central lumen to actuate the work element tips by pushing against the proximal edge of the body portion tab element 458 from within the work element.

Figure 15:
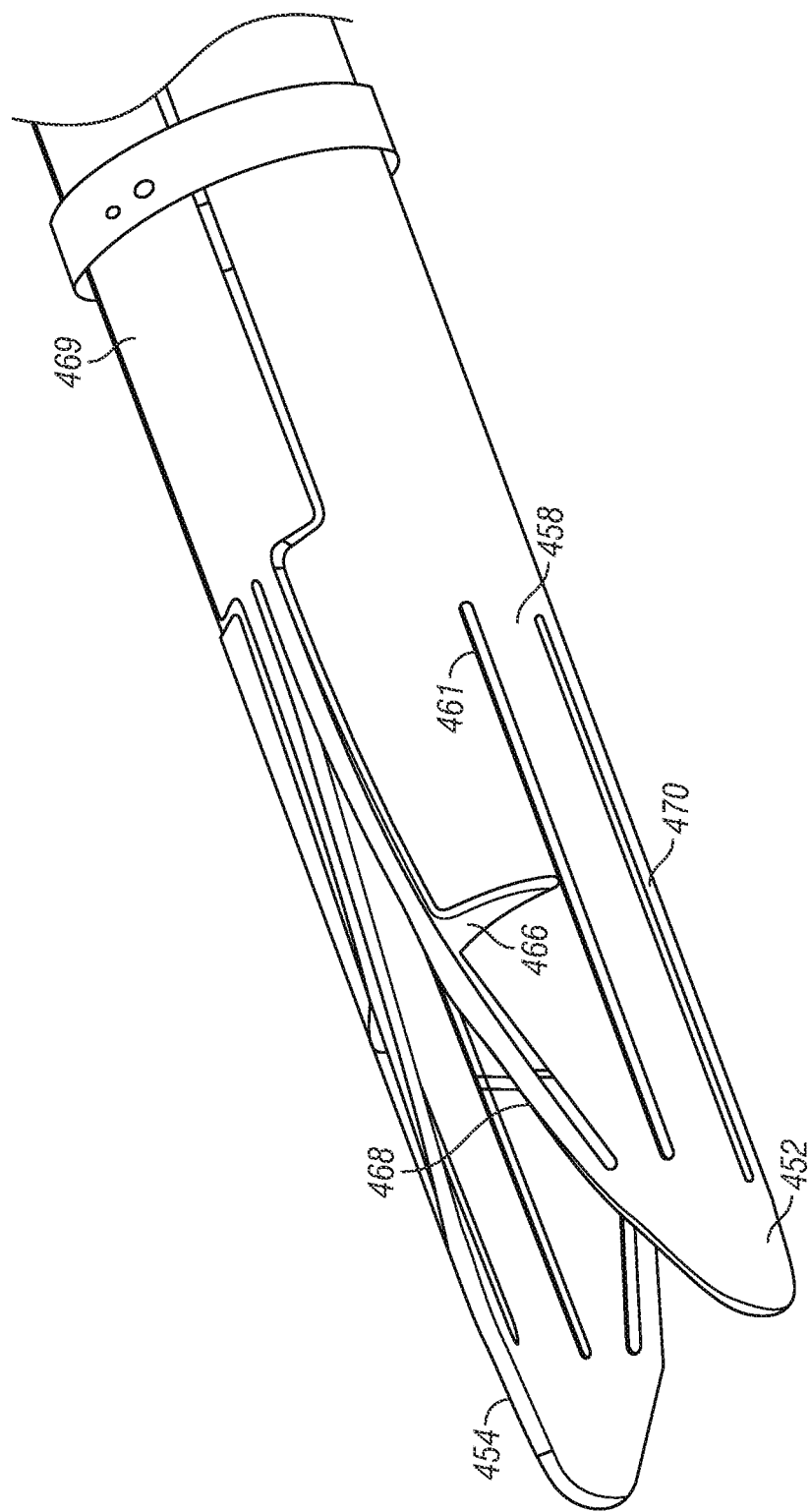
FIG. 15 shows details of a work element, according to one embodiment.

FIG. 15 shows a single tube work element as a monolithic structure, but differing from that of FIGS. 14A and 14B, according to one embodiment. In this figure, it should be noted that the tip 452 or tips 452/454 (as shown, but a single tip would function under the principles discussed herein, or an articulable tip acting against a fixed opposite tip would also be fully functioning, according to embodiments) are joined through tendon(s) 468/470 to a tendon actuation tab 469 (as opposed to a body portion actuation tab element 458 of FIG. 14B) and the tendon actuation tab 469 is attached to a collar 532. A force such as force 462 of FIG. 14A acting on the collar 532 would pull the tendon(s) 468/470 in a proximal direction, forcing the living hinge shown at 458 in this figure to flex and thus close the tip(s) against each other, or flex the single tip into the central lumen, or close one articulable tip against an opposite fixed tip, according to various embodiments. As shown, the forces acting against the tip or tips in this figure are similar to, but distinctly different from, in application, the embodiment of FIG. 14A. In this case, the tendons are pulled distally, pulling the tip(s) inward, whereas in FIG. 14A, the tendons are fixed and the body portion extension tab 458 is pushed distally to pull the tip(s) of that embodiment inward. While the net result is that the tip(s) close as a result of relative axial motion between portions of the single tube structures in each embodiment, the two configurations may be combined as discussed below to form a complex work element with a simple activation mechanism, according to a further embodiment.

In further embodiments, a single scoopula of an outer device of FIG. 14A, combined with an inner device of FIG. 15, may allow for the inner beak, in the example cited, to nest into the outer already flexed scoopula, which may be advantageous if the outer scoopula work element is used as a downstream barrier while the inner beak work element acts to remove or dislodge material upstream from that point and from, for example, the lumen of an artery. Such an embodiment may also be advantageous, as will be illustrated later, to grasp both edges of an arterial obstruction simultaneously while still allowing one or both work elements to rotate independently of the other. A distal axial pushing of an inner element, such as that shown in FIG. 15 against the end of the tendon actuation element proximal to element 701 of the embodiment of FIG. 14B, would result in both work elements closing and morcellating, in a manner similar to the combined jackhammer-morcellation action described above for FIGS. 14A and 14B with an outer tube of FIG. 8. According to one embodiment, a third independent work element, which may comprise a coring excisional device, may also be introduced down the central lumen of the complex work element discussed in this paragraph. In such a method, the complex work element, with its independent work elements, could serve as a complete shield and isolate an inner work area between the two work elements, while a third coring or excisional work element is introduced to selectively retrieve material in the central lumen of such an artificially-created work area, thus protecting sensitive subjacent arterial wall structures from the actions of the excisional work element. Any debris dislodged by the coring or excisional process of the excisional device may then be contained within the work area defined by the complex work element described above, according to embodiments.

Figure 16:
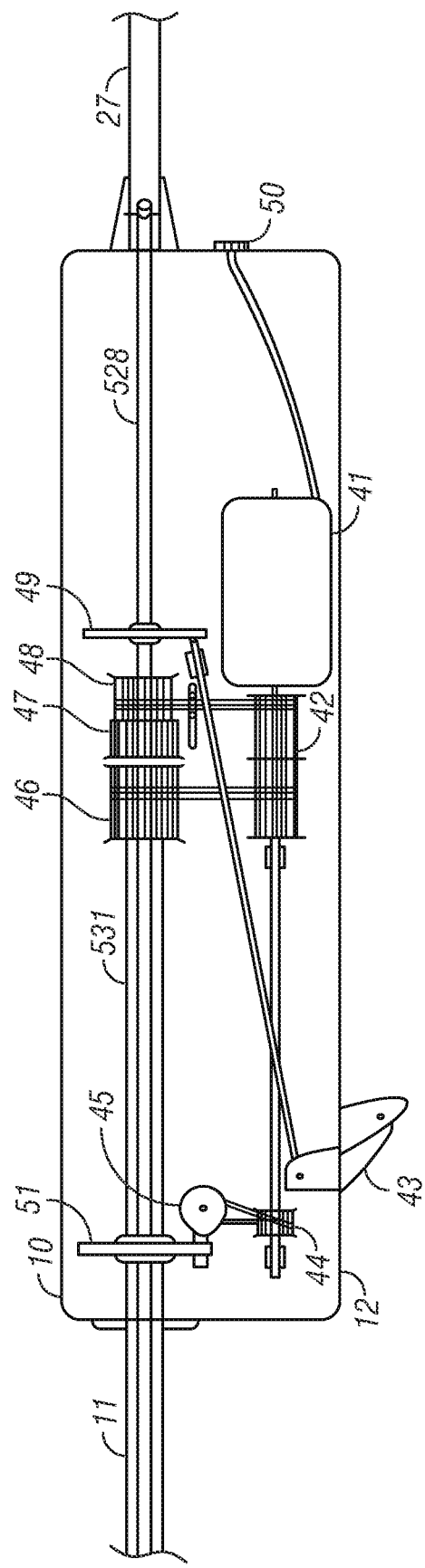
FIG. 16 shows details of a driving mechanism, according to one embodiment.

FIG. 16 shows details of a driving mechanism providing various operating structure and functionalities to the work element described above in FIGS. 9A and 9B, according to one embodiment. This illustration is deliberately simplified for purposes of discussing various modes of operation of a device 10. Illustrated in this figure are the handle 12, a transfer magazine 27, the tubular coring and transport assembly 11, an electric motor 41, a combined inner/outer tube pinion 42 and drive belts, a manual beak closure trigger 43 with its link, a jackhammer function pinion gear 44 with its drive belt, a jackhammer function sliding cam 45, an outer tube driven gear 46, a synchronous inner tube pinion gear portion 47, an asynchronous inner tube pinion gear portion 48, an inner tube thrust bearing/plate assembly 49, an electric connection 50, and an outer tube thrust bearing/plate assembly 51. Using the examples cited for previous figures above, it may be envisioned that periodic pushing on the distal or outer tube 531, according to embodiments, may produce a jackhammer motion induced, in this case, by the jackhammer function sliding cam 45 being brought into close proximity with and acting upon the outer tube thrust bearing/plate assembly 51, either with the tubular coring and transport assembly 11 (inner and outer tubes) rotating or stationary. This function may be manually selected by the operator at any time. If the drive belt associated with the synchronous/asynchronous inner tube pinion gear portions 47 and 48, respectively, is manually slid towards the synchronous portion 47, the inner tube and outer tube will rotate in synchronicity, and the beaks will remain in the position in which they were found when that action is accomplished—either open, closed, or partially open. If, however, the drive belt is slid towards the asynchronous portion 48 of that pinion gear, the inner tube will rotate in asynchronicity with the outer tube, and the beaks will cycle open and closed, or partially opening and closing with a morcellation action, as described in FIGS. 9A and 9B above. This choice may therefore also be manually selected by the operator to induce that desired action at any time. Similarly, if the operator desires, at any time, to manually close the beaks, that may be accomplished by pressing on the beak closure trigger 43, which in turn presses the link abutting the inner tube thrust bearing/plate assembly 49. It should be noted, therefore, that either differential rotational motion or pulling proximally on the inner or proximal tube 528 (by action of the trigger 43 with its link pushing it in a proximal direction), according to embodiments, actuates the beaks to partially or fully open and close, including a manual beak closing action, as may be desired by an operator. Such an embodiment, as illustrated simply herein, enables full functioning of the device 10 according to a multiplicity of desired modes of operation, which may be selected at any time by an operator to attack different segments of a chronic total occlusion, for example, and according to methods. Although the embodiment illustrated herein shows a mechanical system capable of inducing the various desired movements to the work element, it is shown for illustrative purposes only and one skilled in the art will understand that any number of common driving elements and work elements described herein may be combined to accomplish the same purposes, all of which are considered to be within the scope of this disclosure.

As may be inferred by the elements of the driving mechanism of FIG. 16 above, the following exemplary selectable modes of operation of a device 10 may be envisioned, according to various methods and embodiments:

Beaks open and coring under rotation without morcellation;

Beaks open and coring under rotation without morcellation but with jackhammer puncturing action;

Beaks cyclically morcellating under rotation with jackhammer puncturing action;
Beaks cyclically morcellating under rotation without jackhammer puncturing action;
Beaks closed and penetrating under rotation with jackhammer puncturing action;
Beaks closed and penetrating under rotation without jackhammer puncturing action;
Beaks closed and penetrating with jackhammer puncturing action without rotation;
Beaks closed and penetrating without jackhammer puncturing action and without rotation;
Any of the above modes with or without manual beak opening and closure, and/or with or without either or both flush and vacuum at any time within a given operating mode.

Since the complete range of selectable options listed above is available to an operator to pass through and capture the occluding material, an operator is not limited to a single mode for an entire procedure, according to methods herein. It may typically be found, for example, that once a hard cap of an occlusion has been passed that the occluding material may be softer and simple open beak coring may be desired with an operator selected core length to capture and transport occluding material out of the body, for example and according to one method.

According to embodiments, one method of clearing a total chronic occlusion may include advancing a guide wire to the face of such an occlusion, the guide wire being furnished with a guidance modality such as OCT, fiber optic camera element or ultra-sound transponder, and even with a Geiger counter for certain soft tissue biopsy requirements, for example. Once the guide wire is in place, work element 13 may be advanced over the guide wire to the forward face of the occlusion. The excisional work element of the device may be used to attack the hard cap of the occlusion with high speed cutting and coring under rotation or using any of the operating modes described above, as selected by an operator. Alternatively, work element 13 may be introduced within the structure of a separate work element, for example containing scoopula or beak structures to grip and anchor the sides of the occlusion's typically hard cap, followed by a range of optional procedures. All such procedures are now available due to the establishment of access to the occlusion while protecting the subjacent arterial wall structure. Once the hard occlusion cap has been penetrated and removed, the device comprising work element 13 may be incrementally advanced, with or without incremental scoopula closures in varying degrees at various steps, which may be useful in incrementally isolating portions of the occlusion to be removed and thus preventing debris from flushing downstream and avoiding complications due to embolic results caused by loose debris.

Figure 17:
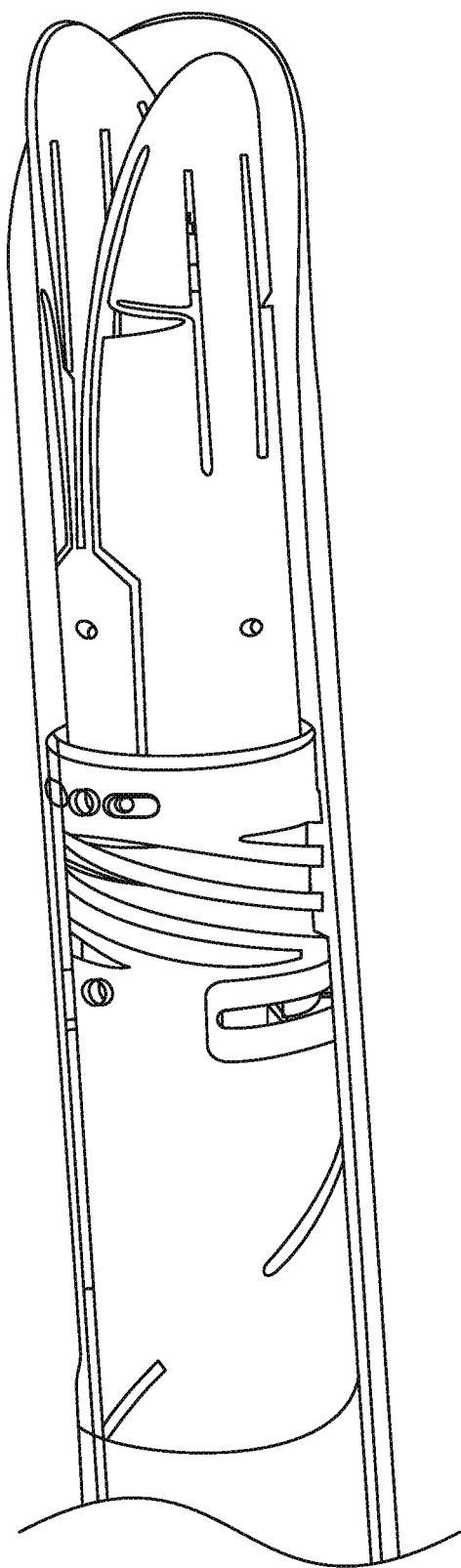
FIG. 17 is a representation of an innermost monolithic structure comprising a pair of beaks, a middle tubular/helical structure and an outermost tubular scoopula, according to one embodiment.

Represented in FIG. 17 is a rendition of a twin-beak device (based on a double beak coring/part-off assembly in relationship with a scoopula component) showing the two beaks in red in the innermost position within a middle element (grey tubular/helical element) a scoopula (brown, outermost element), and shown in distal position where they are about to be closed to part-off tissue that they have cored while rotating and traveling proximal to distal in the scoopula, in their wide open configuration. The mechanism for opening them and keeping them open throughout their proximal to distal excursion involves rotating the grey outer sheath (outer with respect to the inner red tube and/or helical element, inner relative to the non or differentially rotating outer scoopula) in a counter clockwise direction, together with and after holding back the rotation of the inner element (red) only a matter of degrees such that its helical element, which nests into similar helical elements in the grey component, is driven back proximally, after which the two tubular/helical elements (inner, red and middle, brown) rotate together until closure is desired. In this example, the living backbone element is of one structure with its helical component ("threaded" section, nesting in a similar component in the middle tubular/helical "threaded" section) and has limited travel ability that comprises both rotation relative to the middle tubular/helical structure and longitudinal (linear) movement. Because the keystone element of the red beak component(s) is constrained such that it may only move in a circular slot in the middle (grey) tubular/helical structure, which is at a finer pitch (shown here as 90 degrees to the long axis), the beaks necessarily open wide based on the relative linear motions imposed on keystone (attached to living tendons) and living backbone. Upon reaching the part-off region, (or at any time part-off or other reason to close the beak elements is desired) the inner-most tube/helix is made to "catch up" while rotating, to the middle (grey) tubular/helical element thus causing the threaded elements of each of the tubular/helical components that are threaded with each other, to return to the resting or "closed" configuration and force a linear motion, again based on the fact that the keystone element is constrained to only move at a finer pitch (in this case approximately 90 degrees to the long axis of the roughly tubular elements) than those of the threaded elements to fully close the beaks.

Figure 18:
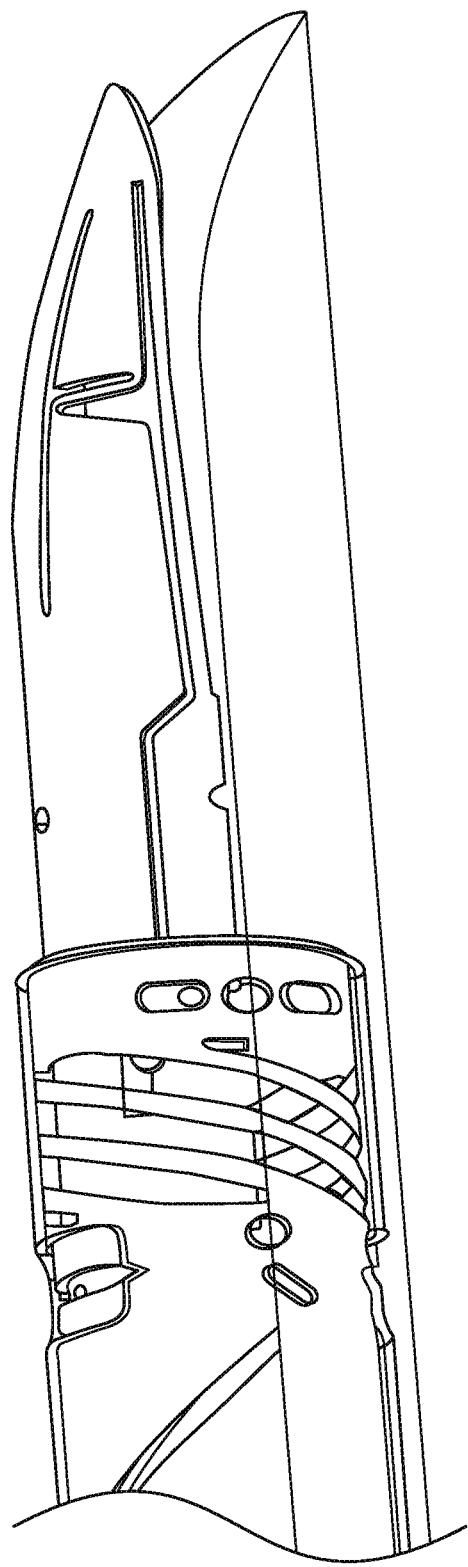
FIG. 18 is a representation of an innermost tubular/helical structure comprising a beak and components shown, a middle tubular/helical structure and an outer scoopula, according to one embodiment.

FIG. 18 shows a single beak variant based on the same principles as the above example shown with two beaks. In this instance, the beak is already at a point where it is desirable to have it close down against the inner surface of the scoopula for purposes of parting-off a cored specimen or for penetration to approach a target or for other purposes such as to deliver a substance or element to a site without allowing ingress of tissue during the approach to a target. In this case the rotating inner (blue) tubular/helical structure will have been made to "catch up" (briefly accelerated in rotation) with respect to the also rotating middle tubular/helical structure (grey) closing the beak down against the scoopula (tan) element. At that point rotation may be completely halted for beak retraction and transport of cored specimen(s) and the entire sequence repeated as often as desired.

The described embodiments may be formed of or comprise one or more biocompatible materials such as, for example, stainless steel or other biocompatible alloys, and may be made of, comprise or be coated with polymers and/or biopolymer materials as needed to optimize function(s). For example, the cutting elements (such as the constituent elements of a work element 13) may comprise or be made of hardened alloys or carbon fiber or other polymers or plastics, and may be additionally coated with a slippery material or materials to thereby optimize passage through living tissues of a variety of consistencies and frictions. Some of the components may be purposely surface-treated differentially with respect to adjacent components, as may be inferred herein in reference to a transporting tubular and storage component (not shown). The various internal or external components may be made of any suitable, commercially available materials such as nylons, polymers such as moldable plastics, and others. The handle may be configured in such a way as to make it easily adaptable to one of any number of existing guiding platforms, such as stereotactic table stages. The materials used in the present material delivery or removal device may also be carefully selected from a Ferro-magnetic standpoint, such that the present material delivery or removal device maintains compatibility with magnetic resonance imaging (MRI) equipment that is commonly used for material delivery or removal procedures. Vacuum/delivery assembly components may comprise commercially available vacuum pumps, syringes and tubing for connecting to the present material delivery or removal device, along with readily available reed valves for switching between suction and emptying of materials such as fluids which may be suctioned by vacuum components. The fluids collected by the embodiments of the present device in this manner may then be ejected into an additional external, yet portable, liquid storage vessel connected to the tubing of the present device, for safe keeping and laboratory cellular analysis.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the figures. Depending on the embodiment, certain steps described in the example above may be removed, and others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

The invention claimed is:

1. An excisional device, comprising:
   a tubular coring and transport assembly comprising an inner tube and an outer tube that is co-axially disposed relative to the inner tube;
   a work element coupled to the tubular coring and transport assembly and configured to cut tissue by selectably assuming an open configuration, a closed configuration or intermediate configurations between the open and closed configurations;
   a handle disposed away from the work element and comprising a driving assembly comprising:
   an electric motor;
   an inner and outer tube pinion coupled to the inner tube and driven by the electric motor;
   an outer tube driven gear coupled to the outer tube and driven by the inner and outer tube pinion by a first drive belt;
   an asynchronous inner tube pinion gear selectably driven by the inner and outer tube pinion by a second drive belt; and
   a synchronous inner tube pinion gear selectably driven by the inner and outer tube pinion by the second drive belt and disposed between the asynchronous inner tube pinion gear and the outer tube driven gear;
   wherein when the second drive belt is disposed so as to drive the synchronous inner tube pinion gear, the inner tube and the outer tube rotate synchronously, and
   wherein when the second drive belt is disposed so as to drive the asynchronous inner tube pinion gear, the inner tube and the outer tube rotate asynchronously.

2. The device of claim 1, wherein when the second drive belt is disposed so as to drive the synchronous inner tube pinion gear and the inner tube and the outer tube rotate synchronously, the work element remains in one of the closed configuration, the open configuration and one of the intermediate configurations.

3. The device of claim 1, wherein when the second drive belt is disposed so as to drive the asynchronous inner tube pinion gear and the inner tube and the outer tube rotate asynchronously, the work element cycles between the closed configuration, the intermediate configurations and the open configuration.

4. The device of claim 1, wherein the driving assembly further comprises:
   a manual work element closure trigger; and
   an inner tube thrust bearing plate assembly coupled to the inner tube,
   wherein actuation of the manual work element closure trigger acts upon the inner tube thrust bearing plate assembly to pull the inner tube in a proximal direction and causes the work element to assume the closed configuration.

5. The device of claim 4, wherein the driving assembly further comprises:
   a jackhammer function pinion gear driven by the inner and outer tube pinion;
   a jackhammer function sliding cam driven by the jackhammer function pinion gear by a third drive belt; and
   an outer tube thrust bearing plate assembly coupled to the outer tube;
   wherein the jackhammer function sliding cam is configured to be cyclically brought into contact with and act upon the outer tube thrust bearing plate assembly to induce a jackhammer motion on the work element to puncture tissue.

6. The device of claim 5, wherein the inner and outer pinion is configured to selectively entrain the work element in rotation and wherein the jackhammer motion is selectively induced when the work element is entrained in rotation or stationary.

7. The device of claim 5, wherein the driving assembly further comprises:
   a first collar element coupled to the inner tube and a second collar element coupled to the outer tube, the first collar element comprising a first peripheral surface that extends around the first collar element and that faces a proximal end of the device and the second collar element comprising a second peripheral surface that that extends around the second collar element, faces a distal end of the device and at least partially contacts the first peripheral surface,
   wherein the first peripheral surface is a smooth surface that comprises a plurality of first peaks and a plurality of first valleys and the second peripheral surface is a smooth surface that comprises a plurality of second peaks and a plurality of second valleys, and
   wherein the inner tube, the outer tube and the first and second collars are configured to control opening, closing, extending and retracting the work element by at least one of rotating in synchronously by causing the second drive belt to drive the synchronous inner tube pinion gear, rotating asynchronously by causing the second drive belt to drive the asynchronous inner tube pinion gear, and differentially moving the inner and outer tubes in an axial direction.

8. The device of claim 7, wherein the driving assembly and the work element are selectably configurable to cause modes of operation including:
   the work element assuming the open configuration and core through tissue under rotation without opening and closing to morcellate tissue;
   the work element assuming the open configuration and core through tissue under rotation without morcellation but with the jackhammer motion;
   the work element cyclically morcellating tissue under rotation with the jackhammer motion;
   the work element cyclically morcellating tissue under rotation without the jackhammer motion;
   the work element assuming the closed configuration under rotation with the jackhammer motion;
   the work element assuming the closed configuration under rotation without the jackhammer motion;
   the work element to assuming the closed configuration without rotation and with the jackhammer motion; and
   the work element to assuming the closed configuration without rotation and without the jackhammer motion.

9. The device of claim 8, wherein the driving assembly and the work element are further selectably configurable to cause any of the modes of operation with or without actuation of the manual work element closure trigger and/or with or without flush and/or vacuum.

* * * * *